United States Patent
Ju et al.

(10) Patent No.: US 10,696,993 B2
(45) Date of Patent: Jun. 30, 2020

(54) ENZYME BASED METHODS OF SEPARATING PROTEIN FROM PROTEIN-RICH MATERIAL

(71) Applicants: Lu-Kwang Ju, Akron, OH (US); S M Mahfuzul Islam, Akron, OH (US); Qian Li, Akron, OH (US); Abdullah Al Loman, Akron, OH (US)

(72) Inventors: Lu-Kwang Ju, Akron, OH (US); S M Mahfuzul Islam, Akron, OH (US); Qian Li, Akron, OH (US); Abdullah Al Loman, Akron, OH (US)

(73) Assignee: The University of Akron, Akron, OH (US)

( * ) Notice: Subject to any disclaimer, the term of this patent is extended or adjusted under 35 U.S.C. 154(b) by 62 days.

(21) Appl. No.: 15/133,777

(22) Filed: Apr. 20, 2016

(65) Prior Publication Data
US 2016/0304925 A1    Oct. 20, 2016

Related U.S. Application Data

(60) Provisional application No. 62/149,709, filed on Apr. 20, 2015.

(51) Int. Cl.
*C12P 19/14* (2006.01)
*C12P 19/02* (2006.01)

(52) U.S. Cl.
CPC ............. *C12P 19/14* (2013.01); *C12P 19/02* (2013.01); *Y02P 20/582* (2015.11)

(58) Field of Classification Search
None
See application file for complete search history.

(56) References Cited

U.S. PATENT DOCUMENTS 7,727,746 B2 *  6/2010  Foody .................. C12P 19/02
                                                     435/105

FOREIGN PATENT DOCUMENTS

WO    WO-2013170017 A2 *  11/2013  ............. A23J 1/148

OTHER PUBLICATIONS

Long, Craig C; Gibbons, William R; "Conversion of soy molasses, soy solubles, and dried soybean carbohydrates into ethanol" International Journal of Agricultural and Biological Engineering, 6,. 62-68, 2013) (Year: 2013).*

Suwannarangsee, Surisa; et al; "Production and Characterization of Multi-Polysaccharide Degrading Enzymes from Aspergillus aculeatus BCC199 for Saccharification of Agricultural Residues" Journal of Microbiology and Biotechnology, 24, 1427-1437, 2014 ( Year: 2001).*

Longobardi, GP; "Fed-Batch versus Batch Fermentation" Bioprocess Engineering, 10, 185-194, 1994 (Year: 1994).*

(Continued)

*Primary Examiner* — David W Berke-Schlessel
(74) *Attorney, Agent, or Firm* — Renner, Kenner, Greive, Bobak Taylor &- Weber Co., L.P.A.

(57) ABSTRACT

Improved enzyme based methods of separating protein from protein-rich material are provided. A method can include utilizing a modeling equation to more effectively hydrolyze the various types of carbohydrates present in a protein-rich material. A method can include a fed-batch method of incrementally adding a protein-rich material, an enzyme broth, or both a protein-rich material and an enzyme broth. A method can also include partially or completely recycling the hydrolysate.

15 Claims, 9 Drawing Sheets

(56) References Cited

OTHER PUBLICATIONS

Eckard, Anahita Dehkhoda; et al; "Enzyme recycling in a simultaneous and separate saccharification and fermentation of corn stover: A comparison between the effect of polymeric micelles of surfactants and polypeptides" Bioresource Technology, 132, 202-209, 2013 (Year: 2013).*

Tu, Maobing; et al; "Evaluating the Distribution of Cellulases and the Recycling of Free Cellulases during the Hydrolysis of Lignocellulosic Substrates" Biotechnology Progress, 23, 398-406, 2007 (Year: 2007).*

Tu, Maobing; et al; "The potential of enzyme recycling during the hydrolysis of a mixed softwood feedstock" Bioresource Technology, 100, 6407-6415, 2009 (Year: 2009).*

Kumar, R. and C.E. Wyman, Effect of xylanase supplementation of cellulase on digestion of corn stover solids prepared by leading pretreatment technologies. Bioresource Technology, 2009. 100(18): p. 4203-4213.

Yang, M., et al., High-concentration sugars production from corn stover based on combined pretreatments and fed-batch process. Bioresource technology, 2010. 101(13): p. 4884-4888.

de Albuquerque Wanderley, M.C., et al., Increase in ethanol production from sugarcane bagasse based on combined pretreatments and fed-batch enzymatic hydrolysis. Bioresource technology, 2013. 128: p. 448-453.

Hamzah, F., A. Idris, and T.K. Shuan, Preliminary study on enzymatic hydrolysis of treated oil palm (Elaeis) empty fruit bunches fibre (EFB) by using combination of cellulase and β 1-4 glucosidase. Biomass and bioenergy, 2011. 35(3): p. 1055-1059.

Hodge, D.B., et al., Model-based fed-batch for high-solids enzymatic cellulose hydrolysis. Applied biochemistry and biotechnology, 2009. 152(1): p. 88-107.

Solis-Pereyra S, Favela-Torres E, Gutierrez-Rojas M, Roussos S, Saucedo-Castaneda G, Gunasekaran P, et al. Production of pectinases by Aspergillus niger in solid state fermentation at high initial glucose concentrations. World J Microbiol Biotechnol 1996;12:257.

Bailey MJ, Buchert J, Viikari L. Effect of pH on production of xylanase by Trichoderma reesei on xylan-and cellulose-based media. Appl Microbiol Biotechnol 1993;40:224.

Mary Mandels and James Weber "The Production of Cellulases" Food Microbiology Division, US Army Natick Laboratories, Natick, Mass. 01760 Cellulases and Their Applications Chapter 23, pp. 391-414.

R. K. Dasari and R. Eric Berson, "The effect of particle size on hydrolysis reaction rates and rheological properties in cellulosic slurries," Appl. Biochem. Biotechnol., vol. 137-140, No. 1-12, pp. 289-299, 2007.

A.-I. Yeh, Y.-C. Huang, and S. H. Chen, "Effect of particle size on the rate of enzymatic hydrolysis of cellulose," Carbohydr. Polym., vol. 79, No. 1, pp. 192-199, 2010.

A. Rosenthal, D. L. Pyle, and K. Niranjan, "Simultaneous Aqueous Extraction of Oil and Protein from Soybean: Mechanisms for Process Design," Food Bioprod. Process., vol. 76, No. 4, pp. 224-230, 1998.

A. Caprita and R. Caprita, "Modification of the soluble protein content of heat-processed soybean flour," Not. Bot. Horti Agrobot. Cluj-Napoca, vol. 38, No. 2, pp. 98-101, 2010.

C. Radha and V. Prakash, "Structural and Functional Properties of Heat-processed Soybean Flour: Effect of Proteolytic Modification," Food Sci. Technol. Int., vol. 15, pp. 453-463, 2009.

\* cited by examiner

ENZYME BASED METHODS OF SEPARATING PROTEIN FROM PROTEIN-RICH MATERIAL

CROSS REFERENCE TO RELATED APPLICATIONS

This application claims the benefit of U.S. provisional patent application Ser. No. 62/149,709 entitled "Highly Effective Enzyme for Soy Processing, Improved Production of Said Enzyme, and Improved Technologies for Enzymatic Soy Processing," filed Apr. 20, 2015, and incorporated by reference in its entirety.

FIELD OF THE INVENTION

The present invention is directed to improved enzyme based methods of separating protein from protein-rich material derived from plant seeds, fruits and other biomass. The present invention is further related to one or more methods of hydrolyzing the various types of carbohydrates present in a protein-rich material utilizing a modeling equation. The present invention is further related to one or more modified batch hydrolysis methods wherein a protein-rich material is incrementally added, or an enzyme broth is incrementally added, or both a protein-rich material and an enzyme broth are incrementally added. The present invention is further related to one or more methods wherein the hydrolysate is partially or completely recycled. The present invention is further related to one or more methods wherein one or more properties of a hydrolysis process are adjusted. The present invention is further related to one or more methods wherein one or more properties of a fermentation process are adjusted.

BACKGROUND OF THE INVENTION

Soybeans are very well known for their high value oil and protein; however, they also contain a significant amount of carbohydrates. These carbohydrates can be hydrolyzed with enzymes. However, various types of carbohydrates are present, making complete hydrolysis of the carbohydrates challenging. Moreover, differing amounts of these types of carbohydrates are hydrolyzable by each enzyme group present in an enzyme broth. The development and production of optimal enzyme mixtures that are capable of hydrolyzing all types of carbohydrates is lacking. Also, the prior art lacks the description of process steps and conditions for achieving high carbohydrate conversion. Therefore, there is a need in the art for improved enzyme based methods for processing plant based materials, such as soy based materials.

SUMMARY OF THE INVENTION

In a first embodiment, the present invention provides a method of hydrolyzing carbohydrates in a protein-rich material comprising the steps of combining a first supply of enzyme broth having an enzyme therein and a first supply of a protein-rich material having carbohydrates therein in a vessel to thereby allow the enzyme to hydrolyze the carbohydrates, adding a further supply to the vessel, the further supply being selected from the group consisting of additional protein-rich material, additional enzyme broth, and both additional protein-rich material and additional enzyme broth, after said step of adding, allowing an additional hydrolysis process to occur.

In a second embodiment, the present invention provides a method as in the first embodiment, wherein the hydrolysis process converts the carbohydrates to soluble carbohydrates, the method further comprising the step of repeating said steps of adding a further supply and allowing an additional hydrolysis process to occur until the conversion of carbohydrates to soluble carbohydrates remains constant.

In a third embodiment, the present invention provides a method as in either the first or second embodiment, the method further comprising the step of repeating said steps of adding a further supply and allowing an additional hydrolysis process to occur until the conversion of the carbohydrates in the protein-rich material to soluble carbohydrates is 65% or higher.

In a fourth embodiment, the present invention provides a method as in any of the first through third embodiments, wherein the enzyme broth further includes a liquid solvent, wherein the liquid solvent is selected from the group consisting of water, sodium citrate buffer, sodium hydroxide, hydrochloric acid, citric acid, ethylene diamine tetra-acetic acid (EDTA), ethanol, methanol, and combinations thereof, wherein the enzyme is selected from the group consisting of cellulase, xylanase, β-glucosidase, cellobiohydrolase, endoglucanase, polygalacturonase, pectinase, pectin lyase, sucrose, α-galactosidase, and combinations thereof.

In a fifth embodiment, the present invention provides a method as in any of the first through fourth embodiments, wherein the further supply includes additional enzyme broth.

In a sixth embodiment, the present invention provides a method as in any of the first through fifth embodiments, further comprising the step of fermenting one or more fungus in a fermentation composition to produce the first supply of enzyme broth, wherein the step of fermenting includes gradually decreasing the pH of the fermentation composition over a predetermined length of time.

In a seventh embodiment, the present invention provides a method of hydrolyzing carbohydrates in a protein-rich material comprising the steps of combining an enzyme broth having an enzyme therein and a protein-rich material having carbohydrates therein to thereby allow the enzyme to hydrolyze the carbohydrates, wherein the hydrolysis results in a product stream, separating the product stream into a protein concentrated stream and a recycled enzyme stream, collecting the protein concentrated stream, and recycling the recycled enzyme stream by combining the recycled enzyme stream with additional protein-rich material and additional enzyme broth.

In an eighth embodiment, the present invention provides a method as in any of the first through seventh embodiments, further comprising the step of collecting a portion of the product stream as a collected hydrolysate stream, such that the recycled enzyme stream is a partially recycled stream.

In a ninth embodiment, the present invention provides a method as in any of the first through eighth embodiments, wherein the product stream is separated into only the protein concentrated stream and a recycled enzyme stream such that the recycled enzyme stream is a complete recycled stream.

In a tenth embodiment, the present invention provides a method as in any of the first through ninth embodiments, wherein said step of combining includes steps of continuously adding the enzyme broth and continuously adding the protein-rich material, the method further comprising the step of continuously removing the product stream.

In an eleventh embodiment, the present invention provides a method as in any of the first through tenth embodiments, wherein the protein-rich material is a soy based material selected from the group consisting of soy flour, soybean meal, soy protein concentrate, soybean hulls, soy flake, white flake, spent soy flake, soybean cake, soybean oil cake, soy molasses, okara, soy pulp, soy bran, soy isolate fiber, and combinations thereof.

In a twelfth embodiment, the present invention provides a method as in any of the first through eleventh embodiments, further comprising the step of fermenting one or more fungus in a fermentation composition to produce the enzyme broth, wherein the step of fermenting includes gradually decreasing the pH of the fermentation composition over a predetermined length of time.

In a thirteenth embodiment, the present invention provides a method as in any of the first through twelfth embodiments, wherein the step of fermenting includes gradually decreasing the pH of the fermentation composition over a first predetermined length of time, maintaining the pH of the fermentation composition at a substantially constant pH for a second predetermined length of time, and gradually decreasing the pH of the fermentation composition over a third predetermined length of time.

In a fourteenth embodiment, the present invention provides a method as in any of the first through thirteenth embodiments, wherein the enzyme is selected from the group consisting of cellulase, xylanase, β-glucosidase, cellobiohydrolase, endoglucanase, polygalacturonase, pectinase, pectin lyase, sucrose, α-galactosidase, and combinations thereof.

In a fifteenth embodiment, the present invention provides a method of hydrolyzing carbohydrates in a protein-rich material comprising the steps of performing a plurality of hydrolysis processes, the hydrolysis processes each including an enzyme broth having an enzyme therein and a protein-rich material having carbohydrates therein, the enzyme broth providing enzyme activity from each of pectinase, xylanase, cellulase, and α-galactosidase, the carbohydrates including a plurality of carbohydrate types therein, wherein the plurality of hydrolysis processes are enacted utilizing varying enzyme mixtures, varying protein-rich material concentrations, and varying ratios of enzyme to protein-rich material, wherein the plurality of hydrolysis processes are each performed using substantially equivalent time, pH, and temperature, determining the conversion of each of the carbohydrate types to both total soluble carbohydrates and reducing sugars for the plurality of hydrolysis processes, and fitting the determined conversions to a model equation to find the best-fit parameters thereof to thereby determine the maximum conversions attainable of each of the carbohydrate types based on the corresponding enzyme activity from each of pectinase, xylanase, cellulase, and α-galactosidase.

In a sixteenth embodiment, the present invention provides a method as in any of the first through fifteenth embodiments, further comprising the step of utilizing the model equation and best-fit parameters to develop a model for kinetic hydrolysis performance.

In a seventeenth embodiment, the present invention provides a method as in any of the first through sixteenth embodiments, further comprising the steps of providing an additional protein-rich material to be hydrolyzed, the additional protein-rich material having various types of carbohydrates therein, and utilizing the model equation and best-fit parameters, and the kinetic hydrolysis performance model, to determine an enzyme mixture that will be capable of effectively hydrolyzing the various types of carbohydrates present in the additional protein-rich material.

In an eighteenth embodiment, the present invention provides a method as in any of the first through seventeenth embodiments, where Formula (1) and Formula (2) are utilized to perform said step of fitting the determined conversions to a model equation, wherein Formula (1) is $$X_{TC} = \frac{TC_S}{TC_0} = \alpha_0 + \frac{\alpha_c \frac{E_c}{S}}{K_c + \frac{E_1}{S}} + \frac{\alpha_x \frac{E_x}{S}}{K_x + \frac{E_x}{S}} + \frac{\alpha_p \frac{E_p}{S}}{K_p + \frac{E_p}{S}} \quad \text{Formula (1)}$$

where $X_{TC}$ is total carbohydrate conversion, $TC_S$ is the total soluble carbohydrate concentration measured in a hydrolysate after a hydrolysis time, $TC_0$ is the total carbohydrate concentration introduced with the protein-rich material, $\alpha_0$ is the fraction of originally soluble carbohydrate in $TC_0$, $\alpha_c$, $\alpha_x$, and $\alpha_p$, are the fractions generated by cellulase, xylanase, and pectinase enzymes, respectively, E represents the activity of each enzyme group, K represents the half-maximum constant for each enzyme activity, where subscripts c, x, and p denote cellulase, xylanase, and pectinase enzymes, respectively, and S represents the total protein-rich material concentration used, and Formula (2) is $$X_{RS} = \quad \text{Formula (2)}$$

$$\frac{RS_S}{TC_0} = \alpha_{0rs} + \frac{\alpha_c \frac{E_c}{S}}{K_c + \frac{E_1}{S}} + \frac{\alpha_x \frac{E_x}{S}}{K_x + \frac{E_x}{S}} + \frac{\alpha_p \frac{E_p}{S}}{K_p + \frac{E_p}{S}} + \frac{\alpha_g \frac{E_g}{S}}{K_g \frac{E_g}{S}}$$

where $X_{RS}$ is the reducing sugar conversion, $\alpha_{0rs}$ is the fraction of soluble monosaccharides in originally soluble portion $\alpha_0$ from Formula (1), $RS_s$ is the reducing sugar concentration measured in a hydrolysate after a hydrolysis time, $TC_0$ is the total carbohydrate concentration introduced with the protein-rich material, $\alpha_c$, $\alpha_x$, $\alpha_p$, and $\alpha_g$ are the fractions generated by cellulase, xylanase, pectinase, and α-galactosidase enzymes, respectively, E represents the activity of each enzyme group, K represents the half-maximum constant for each enzyme activity, where subscripts c, x, p, and g denote cellulase, xylanase, pectinase, and α-galactosidase enzymes, respectively, and S represents the total protein-rich material concentration used.

In a nineteenth embodiment, the present invention provides a method as in any of the first through eighteenth embodiments, where Formula (4) and Formula (5) are utilized to perform said step of utilizing the model equation and best-fit parameters to develop a model for kinetic hydrolysis performance, wherein Formula (4) is $$X_{TC}(\%) = \alpha_0 + k_c \frac{(E_c/S_c)^{m_c}}{S_c^r} t^{\left(0.5-\sqrt{\frac{t}{\tau_{d_c}}}\right)} + \quad \text{Formula (4)}$$

$$k_x \frac{(E_x/S_x)^{m_x}}{S_x^r} t^{\left(0.5-\sqrt{\frac{t}{\tau_{d_x}}}\right)} + k_p \frac{(E_p/S_p)^{m_p}}{S_p^r} t^{\left(0.5-\sqrt{\frac{t}{\tau_{d_p}}}\right)}$$

and Formula (5) is $$X_{RS}(\%) = \alpha_{0rs} + \quad \text{Formula (5)}$$

$$k_c \frac{(E_c/S_c)^{m_c}}{S_c^r} t^{\left(0.5-\sqrt{\frac{t}{\tau_{d_c}}}\right)} + k_x \frac{(E_x/S_x)^{m_x}}{S_x^r} t^{\left(0.5-\sqrt{\frac{t}{\tau_{d_x}}}\right)} +$$

-continued $$k_p \frac{(E_p/S_p)^{m_p}}{S_p^r} t^{\left(0.5-\sqrt{\frac{t}{\tau_{dp}}}\right)} + k_g \frac{(E_g/S_g)^{m_g}}{S_g^r} t^{\left(0.5-\sqrt{\frac{t}{\tau_{dg}}}\right)}$$

where t is time in hours, $\tau_d$ represents a characteristic time which describes how fast the hydrolysis deviates from the initial kinetics, $S_i$ is the concentration of carbohydrate group i, calculated as the fraction of total carbohydrate degradable by enzyme i, r represents the dependency of the enzyme-responsible conversion on the substrate concentration, and k and m are empirical constants, where subscripts c, x, p, and g denote cellulase, xylanase, pectinase, and α-galactosidase, respectively

BRIEF DESCRIPTION OF THE DRAWINGS

Advantages of the present invention will become better understood with regard to the following description, appended claims, and accompanying drawings wherein:

DETAILED DESCRIPTION OF THE ILLUSTRATIVE EMBODIMENTS

Figure 1:
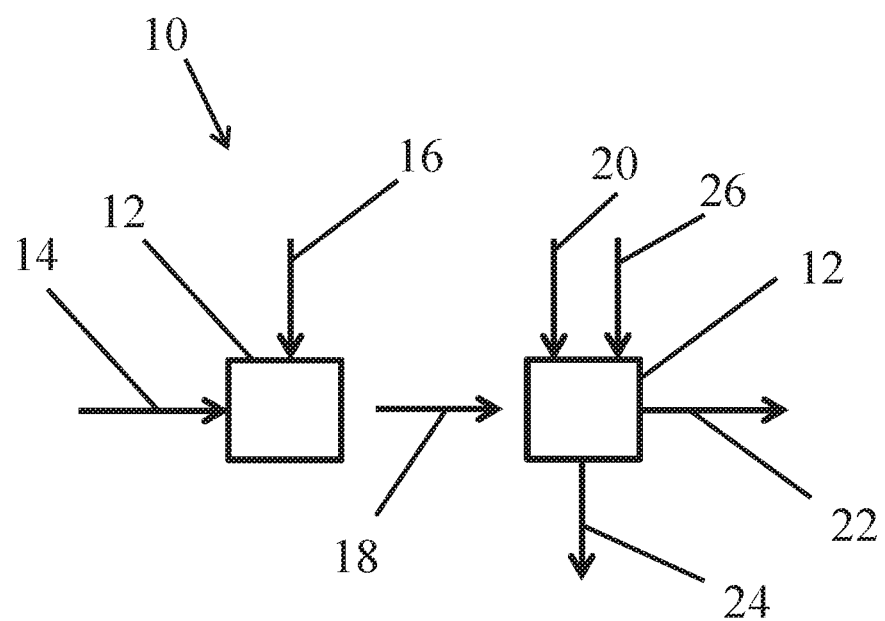
FIG. 1 is a schematic showing a hydrolysis process utilizing fed-batch addition.

The present invention is directed to enzyme based methods for separating protein from protein-rich materials derived from plant seeds, fruit, or other biomass and products made therefrom. The protein content in the resulting products is improved by separating and removing the carbohydrates from around the proteins in the protein-rich materials. Although co-pending application, U.S. Ser. No. 14/400,076, published as US 2015/0118730, which is incorporated fully herein by reference, generally discloses the removal of carbohydrates from protein-rich materials utilizing enzymatic hydrolysis, the present invention includes one or more improved features.

In one or more embodiments, the present invention relates to one or more methods of hydrolyzing the various types of carbohydrates present in soy based materials utilizing a modeling equation. In one or more embodiments, the present invention relates to one or more modified batch hydrolysis methods wherein a soy based material is incrementally added, or an enzyme broth is incrementally added, or both a soy based material and an enzyme broth are incrementally added. In one or more embodiments, the present invention relates to one or more methods wherein the hydrolysate is partially recycled. In one or more embodiments, the present invention relates to one or more methods wherein the hydrolysate is completely recycled. In one or more embodiments, the present invention relates to one or more methods wherein one or more properties of a hydrolysis process are adjusted. In one or more embodiments, the present invention relates to one or more methods wherein one or more properties of a fermentation process are adjusted.

As used herein, protein-rich materials can include any materials derived from plant seeds, fruit, or other biomass, and products made therefrom. Particular protein-rich materials include soy based materials. Soy based materials can be selected from the group consisting of soy flour, soybean meal, soy protein concentrate, soybean hulls, soy flake, white flake, spent soy flake, soybean cake, soybean oil cake, soy molasses, okara, soy pulp, soy bran, soy isolate fiber, and combinations thereof. In one or more embodiments, protein-rich materials can be characterized as those materials having 5% or more protein, in other embodiments, 15% or more protein, and in other embodiments, 40% or more protein.

An enzyme broth, which can also be described as a liquid enzyme medium, can include one or more enzymes and one or more liquid solvents. The enzyme can be selected from the group consisting of cellulase, xylanase, β-glucosidase, cellobiohydrolase, endoglucanase, polygalacturonase, pectinase, pectin lyase, sucrose, α-galactosidase, and combinations thereof. The liquid solvent can be selected from the group consisting of water, sodium citrate buffer, sodium hydroxide, hydrochloric acid, citric acid, Ethylene diamine tetra-acetic acid (EDTA), ethanol, methanol, and combinations thereof. In one or more embodiments, a liquid solvent includes an organic solvent in an aqueous solution. In one or more of embodiments, a liquid solvent includes an organic solvent in an aqueous solution at a percentage of from 15% to 85%, in other embodiments, from 20% to 80%, in other embodiments from 25% to 75%, and in other embodiments, from 30% to 60%.

In one or more embodiments, a liquid enzyme medium is made from the fermentation of one or more fungus selected from the genera consisting of *Trichoderma, Aspergillus, Penicillium, Saccharomyces, Phanerochaete, Rhizopus, Fusarium, Neurospora, Podospora, Pichia,* and *Schizophyllum*. In one or more embodiments, a fungus is selected from the group consisting of *Trichoderma reesei* Rut-C30, *Aspergillus niger* NRRL 322, *Aspergillus niger* NRRL 325, *Aspergillus niger* NRRL 328, *Aspergillus niger* NRRL 334, *Aspergillus niger* NRRL 341, *Aspergillus niger* NRRL 348, *Aspergillus niger* NRRL 363, *Aspergillus niger* NRRL 566, *Aspergillus niger* NRRL 599, *Aspergillus niger* NRRL 2270, *Aspergillus niger* NRRL 13201, *Aspergillus niger* NRRL 13219, *Aspergillus niger* NRRL 62517 and *Aspergillus aculeatus* NRRL 2053, and combinations thereof.

In one or more embodiments, the present invention provides one or more improvements for an enzyme based method for separating protein from protein-rich materials.

In one or more embodiments, an enzyme based method for separating protein from protein-rich materials includes the development of a data fitted model in order to thereafter utilize an enzyme mixture that effectively hydrolyzes all types of carbohydrates present in protein-rich materials. Where the protein-rich materials are one or more soy based materials, hydrolysis of the carbohydrates therein can utilize a complex enzyme system having at least pectinase, xylanase, cellulase, and α-galactosidase activities. For purposes of describing the carbohydrates in soy based materials for the development of a data fitted model, the carbohydrates can be grouped into the groupings of pectin, xylan, cellulose, and oligosaccharides. The carbohydrates can also be grouped into soluble carbohydrates and insoluble carbohydrates, where the solubility is with respect to water.

To obtain a model to enable the development of an enzyme mixture that effectively hydrolyzes all types of carbohydrates present in protein-rich materials, a first step includes running hydrolysis experiments using varying enzyme mixtures, varying protein-rich material concentrations, and varying ratios of enzyme to protein-rich material. These hydrolysis experiments are performed for a predetermined time using a predetermined pH and temperature, and give results for the conversions of the carbohydrates in the protein-rich material to soluble carbohydrates. Soluble carbohydrates in the hydrolysate can be characterized by total soluble carbohydrates, or by the reducing sugars in the soluble carbohydrates, and the conversion for each can be determined.

The enzyme saturation-type model is found using a predetermined hydrolysis time at a predetermined pH and temperature. In one or more embodiments, the hydrolysis time is the time at which total carbohydrate and reducing sugar concentrations no longer increase. In one or more embodiments, the hydrolysis time is the time at which the carbohydrate conversion remains constant, that is when the total carbohydrate and reducing sugar concentrations in the hydrolysate no longer increase. In one or more embodiments, the hydrolysis time is 48 hours. In one or more embodiments, the hydrolysis pH is 4.8. In one or more embodiments, the hydrolysis temperature is 50° C.

The conversions can be found by dividing the total soluble carbohydrates found in the final solution by the total carbohydrate present in the initial protein-rich material. Then, the conversion results can be fit to an enzyme saturation-type model to determine the maximum conversions attainable from the carbohydrate groupings based on the corresponding enzyme activity of each of pectinase, xylanase, cellulase, and α-galactosidase. Thus, the best-fit model parameters can be obtained.

With particular reference now to the equations utilized for developing an enzyme saturation-type model, the total carbohydrate conversion from the hydrolysis experiments is calculated by dividing the total soluble carbohydrate found in the hydrolysate by the total carbohydrate present in the protein-rich material initially added. The soluble carbohydrate found in the hydrolysate include (1) the oligomeric and monomeric carbohydrates that are already water soluble without enzymatic hydrolysis and (2) those that become soluble by the enzymatic degradation of originally insoluble carbohydrate. Accordingly, total carbohydrate conversion can be expressed by the summation of four portions: originally soluble carbohydrate and the three portions solubilized due to hydrolysis by the individual enzymes of cellulase, xylanase, and pectinase, as shown in Formula (1):

$$X_{TC} = \frac{TC_S}{TC_0} = \alpha_0 + \frac{\alpha_c \frac{E_c}{S}}{K_c + \frac{E_1}{S}} + \frac{\alpha_x \frac{E_x}{S}}{K_x + \frac{E_x}{S}} + \frac{\alpha_p \frac{E_p}{S}}{K_p + \frac{E_p}{S}} \quad (1)$$

where $X_{TC}$ is total carbohydrate conversion, $TC_s$ is the total soluble carbohydrate concentration measured in the hydrolysate after the hydrolysis time, and $TC_0$ is the total carbohydrate concentration introduced with the initial protein-rich material. Also, $\alpha_0$ is the portion (fraction) of originally soluble carbohydrate in $TC_0$, and $\alpha_c$, $\alpha_x$, and $\alpha_p$ are the fractions generated by cellulase, xylanase and pectinase enzymes, respectively. E represents the activity of each enzyme group, S represents the total protein-rich material concentration used, and K represents the half-maximum constant for each enzyme activity. Subscripts c, x, and p denote cellulase, xylanase, and pectinase, respectively.

The originally soluble portion ($\alpha_0$) consists of a small fraction of monosaccharides and a majority of oligosaccharides, such as sucrose, stachyose and raffinose. Breaking down these oligosaccharides by α-galactosidase (and sucrase, which is ignored for purposes of the above equation) gives higher reducing sugar concentrations, which frees more reducing ends in the carbohydrate. So, for modeling the reducing sugar conversion ($X_{RS}$), the soluble total carbohydrate portion ($\alpha_0$) can be divided into two portions: soluble monosaccharides ($\alpha_{0rs}$) and the α-galactosidase generated reducing sugars ($\alpha_g$), as given in Formula (2):

$$X_{RS} = \frac{RS_S}{TC_0} = \alpha_{0rs} + \frac{\alpha_c \frac{E_c}{S}}{K_c + \frac{E_c}{S}} + \frac{\alpha_x \frac{E_x}{S}}{K_x + \frac{E_x}{S}} + \frac{\alpha_p \frac{E_p}{S}}{K_p + \frac{E_p}{S}} + \frac{\alpha_g \frac{E_g}{S}}{K_g + \frac{E_g}{S}} \quad (2)$$

where $RS_s$ is the reducing sugar concentration measured in the hydrolysate after the hydrolysis time and the subscript g is used to denote α-galactosidase. The model parameters for cellulase, xylanase, and pectinase are kept the same in both equations. Using these formulas, the maximum fraction of each carbohydrate type can be determined and the basic saturation-type dependency of conversion to the enzyme-to-substrate ratio for each enzyme group can also be fitted.

As a subsequent step, the above equations and determined fitted parameters from the enzyme saturation-type model can be used to develop a model for kinetic hydrolysis performance. That is, conversions can be determined for different hydrolysis times, where these conversions can be fit to a time-dependent model, i.e. a kinetic model.

As elsewhere described herein, increasing the loading of protein-rich material has the general effect of decreasing the achievable carbohydrate conversion. Accordingly, a simple dependency of the enzyme-responsible conversion on the substrate concentration to a negative exponent (r) can be introduced to Formula (3) to describe this negative effect of high protein-rich material concentration:

$$X = A + Bt^{\left(0.5 - \sqrt{\frac{t}{t_d}}\right)} S^{-r} \quad (3)$$

where X is the conversion (%), A is the percentage of readily soluble carbohydrate, t is time (h), B is an empirical constant and is a function of the initial enzyme-to-substrate ratio, S is the substrate concentration, and $\tau_d$ represents a characteristic time which describes how fast the hydrolysis deviates from the initial kinetics.

Then, assuming that each enzyme-carbohydrate group has independent kinetics, the hydrolysis of carbohydrate in protein-rich material can be kinetically modeled using Formulas (4) and (5):

$$X_{TC}(\%) = \alpha_0 + k_c \frac{(E_c/S_c)^{m_c}}{S_c^r} t^{\left(0.5-\sqrt{\frac{t}{\tau_{d_c}}}\right)} + \tag{4}$$

$$k_x \frac{(E_x/S_x)^{m_x}}{S_x^r} t^{\left(0.5-\sqrt{\frac{t}{\tau_{d_x}}}\right)} + k_p \frac{(E_p/S_p)^{m_p}}{S_p^r} t^{\left(0.5-\sqrt{\frac{t}{\tau_{d_p}}}\right)}$$

$$X_{RS}(\%) = \tag{5}$$

$$\alpha_{0rs} + k_c \frac{(E_c/S_c)^{m_c}}{S_c^r} t^{\left(0.5-\sqrt{\frac{t}{\tau_{d_c}}}\right)} + k_x \frac{(E_x/S_x)^{m_x}}{S_x^r} t^{\left(0.5-\sqrt{\frac{t}{\tau_{d_x}}}\right)} +$$

$$k_p \frac{(E_p/S_p)^{m_p}}{S_p^r} t^{\left(0.5-\sqrt{\frac{t}{\tau_{d_p}}}\right)} + k_g \frac{(E_g/S_g)^{m_g}}{S_g^r} t^{\left(0.5-\sqrt{\frac{t}{\tau_{d_g}}}\right)}$$

In Formulas (4) and (5) $S_i$ is the concentration of carbohydrate group i, calculated as the fraction of total carbohydrate degradable by enzyme i, and k and m are empirical constants, where subscripts c, x, p, and g denote cellulase, xylanase, pectinase, and α-galactosidase, respectively. The k constants represent the half-maximum enzyme loading constants for each substrate-enzyme group. All other parameters are as defined herein. The k, m, and $\tau_d$ values in Formulas (4) and (5) may not be the same because, depending on the composition of each enzyme group, breaking down the soluble carbohydrate (measured as total carbohydrate) to monomers, resulting in higher reducing sugar conversions, may be the rate-limiting step. In this case, the kinetic parameters would be different for TC and RS conversions.

Using found experimental results, Formulas (1)-(5) can be model fit with these results to determine the best-fit parameters. Such can be carried out with a non-linear regression optimization procedure, such as is included in the Solver function of the Microsoft Excel program. It should be appreciated that Formulas (4) and (5) are not saturation-type formulas, whereas Formulas (1) and (2) are saturation-type formulas.

For purposes herein, "saturation-type" relates to the point at which the proportionality between increase in conversion and increase in enzyme-to-substrate ratio is diminished. That is, because enzymes catalyze hydrolysis reactions, the more enzyme present, the faster the hydrolysis, and thus, for a given reaction time, the more carbohydrate that is hydrolyzed (i.e. a higher conversion is achieved). But, this proportionality between increase in conversion and increase in enzyme-to-substrate ratio becomes smaller at an increasingly higher enzyme-to-substrate ratio, because the additional enzyme molecules have lower chance to encounter available substrate for them to act on. The proportionality eventually diminishes completely at high enzyme-to-substrate ratios, because all substrate would have been hydrolyzed by the enzyme before the end of the fixed reaction time. Said another way, there's enough enzyme that the reaction is complete before the allocated reaction time. Thus, it can be said that the high enzyme-to-substrate ratios achieve a saturation point.

For model fitting of Formulas (4) and (5), the conversion from each term was limited by the maximum fraction of contribution ($\alpha_c, \alpha_x, \alpha_p, \alpha_g$) of that enzyme group, as obtained from Formulas (1) and (2). An analysis of variance (ANOVA) can then be conducted, such as by using the ANOVA function of the Microsoft Excel program. F and p values can be used to indicate the significance of the developed models. $R^2$ values and adjusted $R^2$ values can be determined to investigate how well the experimental results fit with the model described outcomes. The determined saturation-type formula and kinetic model can then be used to guide the development and production of optimal enzyme mixtures in order to more effectively hydrolyze the various types of carbohydrates present in a protein-rich material. Such can also be used for optimizing the design and operation of a hydrolysis reactor and process.

Once the parameters of a kinetic model are determined, system runs can be performed to test the accuracy of the model. Where a kinetic model under predicts the hydrolysis outcomes of a combination enzyme broth having a mixture of an enzyme broth from a first fungal species and an enzyme broth from a second fungal species, this tends to show a synergistic effect from the combination of the two fungal species. In one or more embodiments, a combination enzyme broth having enzymes of both *A. niger* and *T. reesei* gives a synergistic effect over a predictive kinetic model for a soy flour substrate.

In one or more embodiments, an enzyme based method for separating protein from protein-rich materials includes adjusting the concentration of protein-rich materials in a volume of an enzyme-containing liquid to achieve a higher conversion of the carbohydrates in a protein-rich material to soluble carbohydrates in the resultant hydrolysate. In one or more embodiments, the concentration of protein-rich materials in a volume of an enzyme-containing liquid is lowered in order to achieve a higher conversion to soluble carbohydrate in the resultant hydrolysate.

The concentration of protein-rich material in a volume of an enzyme-containing liquid is the amount of protein-rich material processed in a unit volume of the enzyme-containing liquid. The concentration can be given in units of g/L. This can also be referred to as substrate concentration or solid loading.

Use of a higher concentration achieves a higher concentration of hydrolyzed, soluble carbohydrate in the hydrolysate. Hydrolysate with a higher carbohydrate concentration requires less or no further processing to concentrate for its subsequent use, for example, as fermentation substrate or chemical reactant for production of value-added products. Use of a higher concentration also means a smaller reactor volume and a lower liquid amount are required for processing the same total amount of protein-rich material. A smaller reactor volume translates to a lower capital cost and, potentially, a lower operating cost. The lower liquid amount used translates to less wastewater to handle. But presence of high solid concentrations may increase the viscosity and density of the reaction mixture, making mixing more difficult and more energy-demanding. As discussed further herein, as the concentration of protein-rich material decreases, the conversion to soluble carbohydrates increases. All of these variables might be optimized based on desired operating costs and other economic conditions.

In one or more embodiments, an enzyme based method 10 for separating protein from protein-rich materials includes adding a protein-rich material in multiple batches along the process 10, adding an enzyme in multiple batches along the process 10, or adding both an enzyme and a protein-rich material in multiple batches along the process 10. These methods can be described as fed-batch methods or semi-batch methods.

With reference to FIG. 1, in embodiments where the protein-rich material is added in multiple batches, a first batch of protein-rich material is added to a vessel 12 at arrow 14. The entirety of the enzyme broth is added to vessel 12 at arrow 16. In one or more embodiments, first batch of protein-rich material 14 is added before the entirety of enzyme broth 16. In one or more embodiments, first batch of protein-rich material 14 is added after the entirety of enzyme broth 16. In one or more embodiments, first batch of protein-rich material 14 is added simultaneously with the entirety of enzyme broth 16.

Then, with first batch of protein-rich material 14 and enzyme broth 16 being combined in vessel 12, the one or more enzymes in enzyme broth 16 begin the hydrolysis as to convert the carbohydrates in protein-rich material 14 to soluble carbohydrates. After a predetermined amount of time, indicated by arrow 18, a second batch of protein-rich material is added to vessel 12 at arrow 20. In one or more embodiments, second batch of protein-rich material 20 is added after 3 hours or approximate thereto, in other embodiments, after 6 hours or approximate thereto, and in other embodiments, after 12 hours or approximate thereto. In one or more embodiments, second batch of protein-rich material 20 is added after 3 hours or more, in other embodiments, after 6 hours or more, and in other embodiments, after 12 hours or more. In one or more embodiments, second batch of protein-rich material 20 is added after from 1 hour to 96 hours, in other embodiments, after from 3 hours to 24 hours, in other embodiments, after from 3 hours to 12 hours, and in other embodiments, after from 6 hours to 12 hours.

It should be appreciated that arrow 18 merely indicates the passage of time. That is, in one or more embodiments, the contents of vessel 12 are maintained only in one vessel for the entirety of the hydrolysis. In other embodiments, the contents of vessel 12 can be transferred to another vessel (not shown) before a subsequent batch of protein-rich material is added.

Although only two batches are shown in FIG. 1, it should be appreciated that any number of batches of protein-rich material can be utilized. In one or more embodiments, three batches of protein-rich material are added, in other embodiments, three or more batches of protein-rich material are added, and in other embodiments, more than four batches of protein-rich material are added. In one or more embodiments, each batch of protein-rich material includes 20%, or approximate thereto, of the total protein-rich material to be added, in other embodiments, 25%, or approximate thereto, and in other embodiments, 33⅓%, or approximate thereto.

Following a hydrolysis time, as previously described, the hydrolysis products are separated into two streams: 1) hydrolysate and 2) remaining solids and precipitated protein. For example, the hydrolysate can be collected at arrow 22 and the remaining solids and precipitated protein can be collected at arrow 24.

In one or more embodiments, a method including adding protein-rich material in multiple batches gives a carbohydrate conversion of 45% or higher, in other embodiments, 50% or higher, and in other embodiments, 55% or higher.

With reference again to FIG. 1, in embodiments where the enzyme broth is added in multiple batches, a first batch of enzyme broth is added to vessel 12 at arrow 16. The entirety of the protein-rich material is added to vessel 12 at arrow 14. In one or more embodiments, first batch of enzyme broth 16 is added before the entirety of protein-rich material 14. In one or more embodiments, first batch of enzyme broth 16 is added after the entirety of protein-rich material 14. In one or more embodiments, first batch of enzyme broth 16 is added simultaneously with the entirety of protein-rich material 14.

Then, with first batch of enzyme broth 16 and protein-rich material 14 being combined in vessel 12, the one or more enzymes in enzyme broth 16 begin the hydrolysis as to convert the carbohydrates in protein-rich material 14 to soluble carbohydrates. After a predetermined amount of time, indicated by arrow 18, a second batch of enzyme broth is added to vessel 12 at arrow 26. In one or more embodiments, second batch of enzyme broth 26 is added after 3 hours or approximate thereto, in other embodiments, after 6 hours or approximate thereto, and in other embodiments, after 12 hours or approximate thereto. In one or more embodiments, second batch of enzyme broth 26 is added after 3 hours or more, in other embodiments, after 6 hours or more, and in other embodiments, after 12 hours or more. In one or more embodiments, second batch of enzyme broth 26 is added after from 1 hour to 96 hours, in other embodiments, after from 3 hours to 24 hours, in other embodiments, after from 3 hours to 12 hours, and in other embodiments, after from 6 hours to 12 hours.

Again, it should be appreciated that arrow 18 merely indicates the passage of time. That is, in one or more embodiments, the contents of vessel 12 are maintained only in one vessel for the entirety of the hydrolysis. In other embodiments, the contents of vessel 12 can be transferred to another vessel (not shown) before a subsequent batch of enzyme broth is added.

Although only two batches are shown in FIG. 1, it should be appreciated that any number of batches of enzyme broth can be utilized. In one or more embodiments, three batches of enzyme broth are added, in other embodiments, three or more batches of enzyme broth are added, and in other embodiments, more than four batches of enzyme broth are added. In one or more embodiments, each batch of enzyme broth includes 20%, or approximate thereto, of the total enzyme broth material to be added, in other embodiments, 25%, or approximate thereto, and in other embodiments, 33⅓%, or approximate thereto.

Following a hydrolysis time, as previously described, the hydrolysis products are separated into two streams: 1) hydrolysate and 2) remaining solids and precipitated protein. For example, the hydrolysate can be collected at arrow 22 and the remaining solids and precipitated protein can be collected at arrow 24.

As will be further described herein, a fed batch method utilizing multiple batches of enzyme broth gives higher carbohydrate conversion over a control batch process. Also, a fed batch method utilizing multiple batches of enzyme broth unexpectedly gives higher carbohydrate conversion over a fed batch process utilizing multiple batches of protein-based material. This was unexpected because other known processes including adding all substrate at the beginning tend to result in negative effects. The high concentrations of certain substrates inhibit the health or growth of cells or the activity of enzyme, known as "substrate inhibition," "substrate repression," or "catabolite repression," for different mechanisms and systems. Thus, the beneficial results from a fed batch method utilizing multiple batches of enzyme broth were unexpected.

In one or more embodiments, a method including adding enzyme broth in multiple batches gives a carbohydrate conversion of 60% or higher, in other embodiments, 65% or higher, and in other embodiments, 70% or higher. In one or more embodiments, a method including adding enzyme broth in multiple batches gives a carbohydrate conversion of 72%, or approximate thereto. In one or more embodiments, a method including adding enzyme broth in multiple batches gives a carbohydrate conversion of 4% or more than a control batch method, in other embodiments, 5% or more, and in other embodiments, 7% or more.

With reference again to FIG. 1, in embodiments where both the protein-rich material and enzyme broth are added in multiple batches, a first batch of protein-rich material is added to vessel 12 at arrow 14 and a first batch of enzyme broth is added to vessel 12 at arrow 16. In one or more embodiments, first batch of protein-rich material 14 is added before first batch of enzyme broth 16. In one or more embodiments, first batch of protein-rich material 14 is added after first batch of enzyme broth 16. In one or more embodiments, first batch of protein-rich material 14 is added simultaneously with first batch of enzyme broth 16.

Then, with first batch of protein-rich material 14 and first batch of enzyme broth 16 being combined in vessel 12, the one or more enzymes in enzyme broth 16 begin the hydrolysis as to convert the carbohydrates in protein-rich material 14 to soluble carbohydrates. After a predetermined amount of time, indicated by arrow 18, a second batch of protein-rich material is added to vessel 12 at arrow 20 and a second batch of enzyme broth is added to vessel 12 at arrow 26. In one or more embodiments, second batch of protein-rich material 20 and second batch of enzyme broth 26 are added after 3 hours or approximate thereto, in other embodiments, after 6 hours or approximate thereto, and in other embodiments, after 12 hours or approximate thereto. In one or more embodiments, second batch of protein-rich material 20 and second batch of enzyme broth 26 are added after 3 hours or more, in other embodiments, after 6 hours or more, and in other embodiments, after 12 hours or more. In one or more embodiments, second batch of protein-rich material 20 and second batch of enzyme broth 26 are added after from 1 hour to 96 hours, in other embodiments, after from 3 hours to 24 hours, in other embodiments, after from 3 hours to 12 hours, and in other embodiments, after from 6 hours to 12 hours.

Again, it should be appreciated that arrow 18 merely indicates the passage of time. That is, in one or more embodiments, the contents of vessel 12 are maintained only in one vessel for the entirety of the hydrolysis. In other embodiments, the contents of vessel 12 can be transferred to another vessel (not shown) before subsequent batches of protein-rich material and enzyme broth are added.

Although only two batches are shown in FIG. 1, it should be appreciated that any number of batches of protein-rich material and enzyme broth can be utilized. In one or more embodiments, three batches of protein-rich material and enzyme broth are added, in other embodiments, three or more batches of protein-rich material and enzyme broth are added, and in other embodiments, more than four batches of protein-rich material and enzyme broth are added. In one or more embodiments, each batch of protein-rich material and enzyme broth includes 20%, or approximate thereto, of the total protein-rich material and enzyme broth material to be added, in other embodiments, 25%, or approximate thereto, and in other embodiments, 33⅓%, or approximate thereto.

Following a hydrolysis time, as previously described, the hydrolysis products are separated into two streams: 1) hydrolysate and 2) remaining solids and precipitated protein. For example, the hydrolysate can be collected at arrow 22 and the remaining solids and precipitated protein can be collected at arrow 24.

As will be further described herein, a fed batch method utilizing multiple batches of both enzyme broth and protein-rich material gives higher carbohydrate conversion over a control batch process. Also, a fed batch method utilizing multiple batches of both enzyme broth and protein-rich material unexpectedly gives higher carbohydrate conversion over a fed batch process utilizing multiple batches of protein-based material. This was unexpected because other known processes including adding all substrate at the beginning tend to result in negative effects. The high concentrations of certain substrates inhibit the health or growth of cells or the activity of enzyme, known as "substrate inhibition," "substrate repression," or "catabolite repression," for different mechanisms and systems. Thus, the beneficial results from a fed batch method utilizing multiple batches of both enzyme broth and protein-rich material were unexpected.

In one or more embodiments, a method including adding enzyme broth and protein-rich material in multiple batches gives a carbohydrate conversion of 60% or higher, in other embodiments, 65% or higher, and in other embodiments, 70% or higher. In one or more embodiments, a method including adding enzyme broth and protein-rich material in multiple batches gives a carbohydrate conversion of 71%, or approximate thereto. In one or more embodiments, a method including adding enzyme broth and protein-rich material in multiple batches gives a carbohydrate conversion of 3% or more than a control batch method, in other embodiments, 4% or more, and in other embodiments, 6% or more. In one or more embodiments, a method including adding enzyme broth and protein-rich material in multiple batches gives a carbohydrate conversion of 7% or more than a control batch method, in other embodiments, 10% or more, and in other embodiments, 13% or more.

As used herein, a batch, such as a first batch, second batch, or additional batch, might also be described as a first supply, second supply, or additional supply. Thus, although the term "batch" is used in certain descriptions herein, it should be appreciated that certain embodiments might be a continuous supply of a material, wherein the continuous supply can be described as including a first supply and an additional supply.

One or more embodiments of the present invention include utilizing one or more of the multiple batch processes described herein as part of a continuous process. One or more embodiments of the present invention include utilizing one or more of the multiple batch processes described herein as part of a semi-continuous process. For example, the material to be added could be continuously or semi-continuously added to a hydrolysis process. At the same time, the resulting products could be continuously or semi-continuously removed from the hydrolysis process. The continuous additions and removals could be the continuous additions and removals of batches of the material, or could be added and removed at a continuous flow rate.

In one or more embodiments, a continuous process includes the use of two or more continuously stirred tank reactors (CSTR) in series. In these embodiments, the initial batch of enzyme or protein-rich material or both is continuously added to the first CSTR and a portion of the reaction mixture in this CSTR is continuously removed into the second CSTR with equal feeding and removal rates to maintain a constant volume of reaction mixture in the first CSTR. To the second CSTR, in addition to the portion of reaction mixture moved from the first CSTR, a second batch of enzyme or protein-rich material or both is continuously added. Again, a portion of reaction mixture in the second CSTR is continuously removed into the next CSTR (or a final product collection vessel, if for a two-stage process). This can be repeated for any number of CSTR's.

In one or more embodiments, a continuous process includes the use of a tubular type reactor. In these embodiments, the initial batch of enzyme or protein-rich material or both is continuously added at one end of the reactor, and the reaction mixture is urged through the tubular reactor to exit at the other end for product collection and separation. The additional batches of enzyme or protein-rich material or both are continuously added at selected points along the tubular reactor.

In one or more embodiments, an enzyme based method for separating protein from protein-rich materials includes utilizing at least a portion of the hydrolysate product of a hydrolysis process as a recycle stream for further hydrolysis. One or more embodiments include the use of a partial recycle stream. One or more embodiments include the use of a complete recycle stream. Before a recycle stream is recycled, it can also be described as a to-be-recycled stream.

Figure 2:
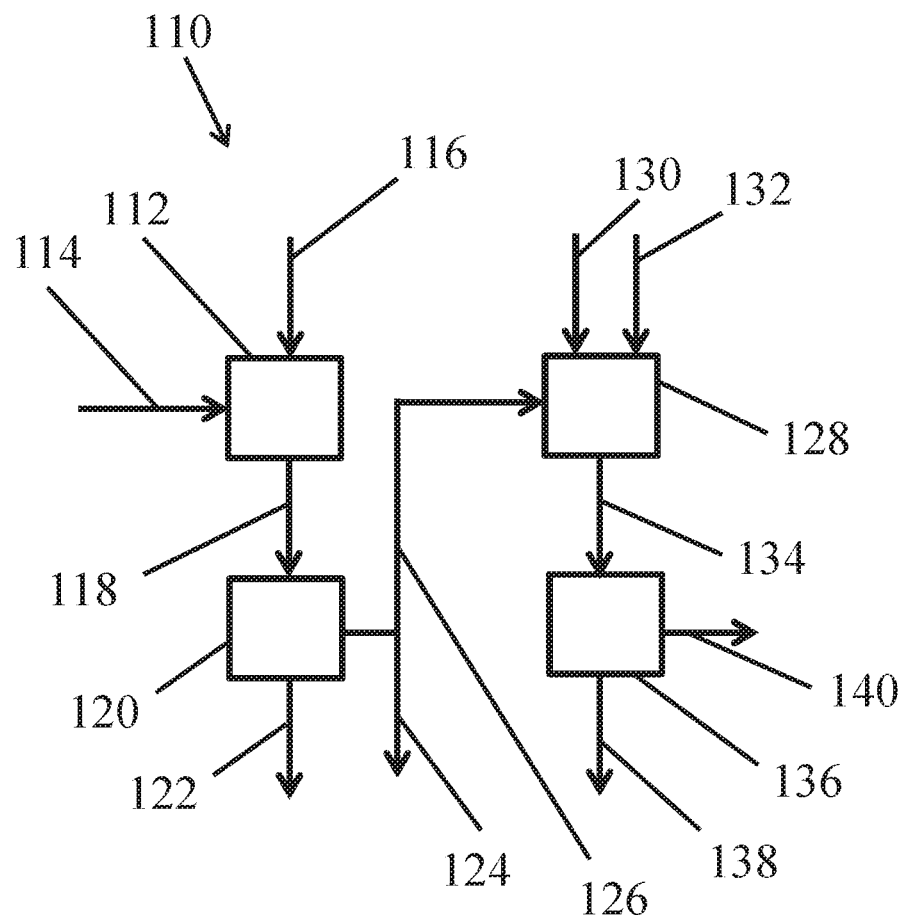
FIG. 2 is a schematic showing a hydrolysis process utilizing partial recycle to an additional vessel.

With reference to FIG. 2, a hydrolysis process 110 utilizing a protein-rich material 114 and an enzyme broth 116 in a vessel 112 gives a product stream 118. Product stream 118 can undergo a separation 120, such as by centrifugation, to result in three streams: protein concentrated stream 122, collected hydrolysate stream 124, and recycled enzyme stream 126. Recycled enzyme stream 126 can then be redistributed to an additional vessel 128, where additional protein-rich material 130 and additional enzyme broth 132 are added. Recycle stream 126 serves to increase the soluble carbohydrate and reducing sugar concentrations of the subsequent hydrolysis process in vessel 128 versus the previous hydrolysis process in vessel 112. Protein concentrated stream 122 is collected and can be processed further, such as by drying to obtain a final solid product or by washing or pressing before drying. Hydrolysis process 110 can be made to be continuous by continuous addition and removal.

Figure 3:
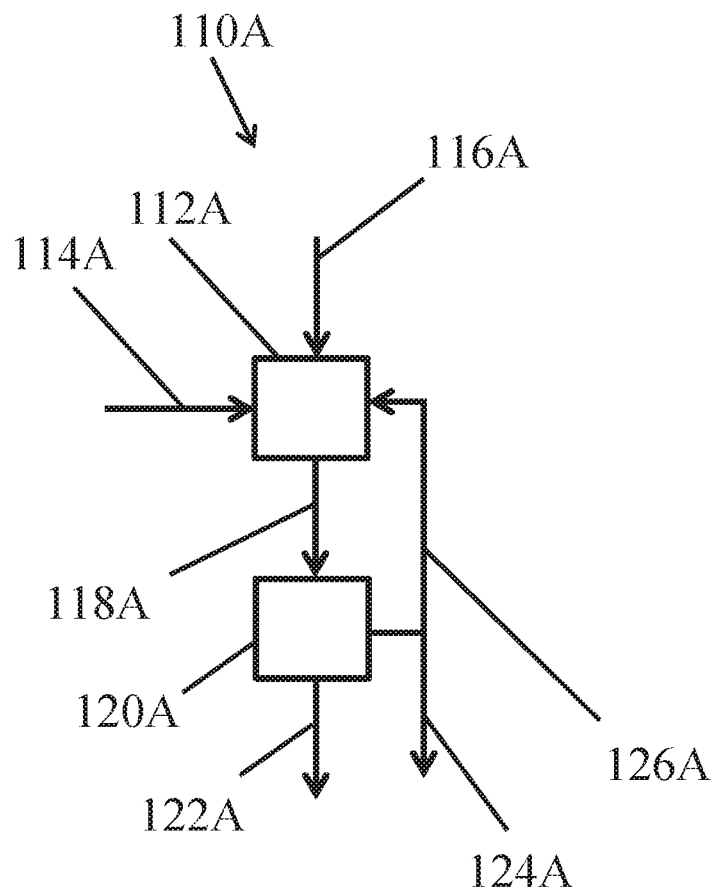
FIG. 3 is a schematic showing a hydrolysis process utilizing partial recycle to the same vessel.

With reference to FIG. 3, a hydrolysis process 110A utilizing a protein-rich material 114A and an enzyme broth 116A in a vessel 112A gives a product stream 118A. Product stream 118A can undergo a separation 120A, such as by centrifugation, to result in three streams: protein concentrated stream 122A, collected hydrolysate stream 124A, and recycled enzyme stream 126A. Recycled enzyme stream 126A can then be redistributed back to 112A, where additional protein-rich material 114A and additional enzyme broth 116A are added. Recycle stream 126A serves to increase the soluble carbohydrate and reducing sugar concentrations of the subsequent hydrolysis process in vessel 112A versus the previous hydrolysis process. Protein concentrated stream 122A is collected and can be processed further, such as by drying to obtain a final solid product or by washing or pressing before drying.

Hydrolysis process 110A can be made to be continuous by continuous addition and removal. For example, protein-rich material 114A, enzyme broth 116A, and recycled enzyme stream 126A are all continuously added into vessel 112A, and product stream 118A is continuously removed from vessel 112A.

In one or more embodiments, multiple recycle steps are utilized. That is, with reference to FIG. 2, subsequent hydrolysis process 128 also can give a product stream 134, which can undergo a separation 136 to result in a protein concentrated stream 138 and a hydrolysate stream 140, which can then be split into a collected hydrolysate stream and a recycled stream. With reference to FIG. 3, a recycle process using the same vessel 112A can include any number of iterations of recycling stream 126A. In either case, the recycle steps can be repeated for any number of partial recycle steps. In one or more embodiments, 2 or more partial recycle steps are utilized, in other embodiments, 3 or more partial recycle steps are utilized, and in other embodiments, 4 or more partial recycle steps are utilized. In one or more embodiments, 5 or more partial recycle steps are utilized, in other embodiments, 6 or more partial recycle steps are utilized, and in other embodiments, 7 or more partial recycle steps are utilized. In one or more embodiments, a number of partial recycle steps are utilized until the soluble carbohydrate and reducing sugar concentrations of a subsequent hydrolysis process is substantially constant with respect to a previous hydrolysis process.

The above described recycle method can be described as a partial recycle process. A portion of the hydrolysate from each hydrolysis process is collected and the remainder is recycled to the next hydrolysis process. A partial recycle process can be characterized by the Formulas (6)-(8):

$$S_n = S_0 + S_0 r + S_0 r^2 + S_0 r^3 + \ldots + S_0 r^n \tag{6}$$

$$S_n = S_0 \left( \frac{1 - r^{n+1}}{1 - r} \right) \tag{7}$$

$$S_{max} = S_0 \left( \frac{1}{1 - r} \right) \tag{8}$$

where $S_n$ is the sugar concentration of the hydrolysate after n amount of recycle steps, r is the recycle rate, and $S_0$ is the sugar concentration of the hydrolysate after a first hydrolysis process without any recycle therein. $S_{max}$ represents the maximum sugar concentration achievable using a specific recycle rate of r. That is, the sugar concentration will not increase above $S_{max}$, even with the use of a further recycle step.

In one or more embodiments, a method including partially recycling hydrolysate gives a total sugar concentration in the final hydrolysate of 60 g/L or higher, in other embodiments, 80 g/L or higher, and in other embodiments, 100 g/L or higher. In one or more embodiments, a method including partially recycling hydrolysate gives a total sugar concentration in the final hydrolysate of 107 g/L, or approximate thereto, and in other embodiments, 109 g/L, or approximate thereto.

Figure 4:
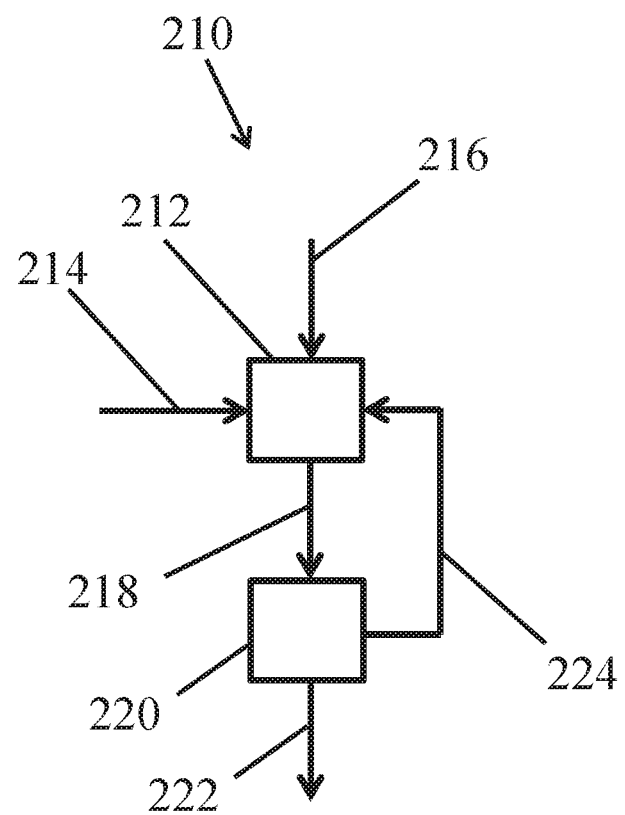
FIG. 4 is a schematic showing a hydrolysis process utilizing complete recycle to an additional vessel.

With reference to FIG. 4, a hydrolysis process 210 utilizing a protein-rich material 214 and an enzyme broth 216 in a vessel 212 gives a product stream 218. Product stream 218 can undergo a separation 220, such as by centrifugation, to result in two streams: protein concentrated stream 222 and recycled stream 224. The entire recycled stream 224 is then utilized for an additional hydrolysis process, where additional protein-rich material 214 and additional enzyme broth 216 are added. Although recycled stream 224 is shown as being recycled back to the same vessel, one or more additional vessels can also be utilized. Protein concentrated stream 222 is collected and can be processed further, such as by drying to obtain a final solid product or by washing or pressing before drying.

Hydrolysis process 210 can be made to be continuous by continuous addition and removal. For example, protein-rich material 214, enzyme broth 216, and recycled enzyme stream 224 are all continuously added into vessel 212, and product stream 218 is continuously removed from vessel 212.

This can be repeated for any number of complete recycle steps. In one or more embodiments, 2 or more complete recycle steps are utilized, in other embodiments, 3 or more complete recycle steps are utilized, and in other embodiments, 4 or more complete recycle steps are utilized. In one or more embodiments, 5 or more complete recycle steps are utilized, in other embodiments, 6 or more complete recycle steps are utilized, and in other embodiments, 7 or more complete recycle steps are utilized. In one or more embodiments, a number of complete recycle steps are utilized until the soluble carbohydrate and reducing sugar concentrations of a subsequent hydrolysis process is substantially constant with respect to a previous hydrolysis process.

In one or more embodiments, a method including complete recycling of hydrolysate gives a total sugar concentration in the final hydrolysate of 40 g/L or higher, in other embodiments, 60 g/L or higher, and in other embodiments, 80 g/L or higher. In one or more embodiments, a method including complete recycling of hydrolysate gives a total sugar concentration in the final hydrolysate of 83 g/L, or approximate thereto.

For any of the above described embodiments, the additional material added for every subsequent batch or for continuous fresh feed can have the same volume as the volume removed. This way, there is no change in total liquid volume in the reactor and the process can be continued indeterminately.

In one or more embodiments, an enzyme based method for separating protein includes adjusting the enzyme strength and enzyme-to-substrate ratio, also known as enzyme loading, to achieve varying concentrations of total soluble carbohydrates and reducing sugars. As used herein, "reducing sugar" can be defined as monomer of sugar molecules with reducing ends and "total soluble carbohydrate" can be defined as all monomeric to oligomeric saccharides that become dissolved in the hydrolysate. Reducing sugar analysis can be made with the dinitrosalicylic (DNS) acid method as generally known to those skilled in the art. The DNS method is generally based on the principle that 3,5-dinitrosalicylic acid is reduced to 3-amino-5-nitrosalicylic acid in the presence of reducing sugar and forms a characteristic color. The reacted colored mixture can be measured for absorbance at 550 nm in a spectrophotometer. Reducing sugar concentration can be determined according to a calibration curve obtained with standard glucose solutions. Total carbohydrate concentrations can be measured using the phenol sulfuric acid colorimetric method as generally known to those skilled in the art. This method is generally based on the principle that all carbohydrate reacts with sulfuric acid to produce furfural derivatives, which then react with phenol to develop a characteristic color. Total carbohydrate concentration can be determined from the absorbance reading according to a calibration curve obtained with standard glucose solutions.

In one or more embodiments, when using a partial recycle process as described herein, a high strength enzyme gives reducing sugar concentration and total carbohydrate concentration that are similar from the very first batch of a recycle system. In contrast, one or more embodiments utilizing a low strength enzyme give a reducing sugar concentration that is initially lower than the total carbohydrate concentration. The reducing sugar concentration then increases with each recycle step. This is believed to be due to low α-galactosidase activity which is insufficient to breakdown the soluble carbohydrates, mainly oligosaccharides (for example, stachyose and raffinose), to reducing sugars. However, with the progression of the recycle, the α-galactosidase activity builds.

As used herein, "a high strength enzyme" can be characterized by the α-galactosidase activity. That is, a ratio of the actual enzyme activity over a modeled constant that is per unit concentration can be determined as a dimensionless enzyme activity of E/K. Using a K value of α-galactosidase of 1.16, the ratio of E/K for "a high strength enzyme" can be characterized as 15 or higher. By "low strength enzyme," it is meant that the enzyme has lower activity than a high strength enzyme, such as an E/K ratio of lower than 12. In one or more embodiments, a high strength enzyme gives similar reducing sugar and total soluble carbohydrate concentrations in from 8 to 10 hours. As the above described E/K ratio is lowered the time until similar reducing sugar and total soluble carbohydrate concentrations will increase. In one or more embodiments, for an E/K ratio of from 10 to 12, the time until similar total carbohydrate and reducing sugar concentrations are achieved is from 12 to 16 hours. In one or more embodiments, the time until similar total carbohydrate and reducing sugar concentrations are achieved is the retention time of one batch.

In one or more embodiments, an enzyme based method for separating protein includes adjusting the recycle rate to achieve varying concentrations of total soluble carbohydrates and reducing sugars. In one or more embodiments, the recycle rate is from 20% to 70%, in other embodiments, from 35% to 55%, and in other embodiments, from 37.5% to 62.5%. In one or more embodiments, the recycle rate is 25%, or approximate thereto, in other embodiments, 37.5%, or approximate thereto, in other embodiments, 50%, or approximate thereto, and in other embodiments, 62.5%, or approximate thereto. In general, a higher recycle rate gives a higher total soluble carbohydrate concentration. But, a higher recycle rate also generally gives lower protein content in the product protein concentrate. Thus, the recycle rate might be optimized based on these parameters of total soluble carbohydrate concentration and protein content in the product protein concentrate, as well as others.

In one or more embodiments, a hydrolysis process utilizing a recycle stream offers one or more benefits compared to a hydrolysis process without a recycle stream. Without a recycle stream, the enzyme added into the reactor is removed, and thus wasted, after the reaction mixture passes through the reactor. With a recycle stream, some of the enzyme previously added is retained in the recycled stream and is added to the reactor to meet the fresh enzyme feed. Thus, enzyme activities accumulate to higher levels than the activities provided in the fresh enzyme feed. This accumulation effect achieved with recycle increases reaction rate, gives higher volumetric productivity, and requires shorter retention time in the reactor.

Also, a hydrolysis process with a recycle stream adjusts and enriches the composition of enzyme actually acting in the reactor. Generally, a fresh enzyme composition includes a complex mixture of enzyme components. Some of these components are more water soluble, such as α-galactosidase, sucrase, β-glucosidase, and the like. While these components are generally responsible for more complete substrate monomerization, these components are often present in insufficient proportions in a fresh enzyme composition because enzyme broths produced by microbial fermentations tend to produce these components in insufficient proportions.

When these components are deficient, more oligomeric compounds are generally produced in the products because their generation from polymer hydrolysis is faster than their removal by further hydrolysis to monomers. These oligomers cause even more indigestibility concerns than the starting polymers because humans and many other animals lack digestive enzymes to break down these oligomers. A hydrolysis process utilizing a recycle stream preferentially retains, recycles, and accumulates the more water-soluble enzyme components than the other components. This is because the other components have higher affinity to adsorb on the solid protein-enriched product stream. Thus, because of the eventual increase in concentration of water-soluble enzyme components in the composition of enzyme actually acting in the reactor, fewer or none of the less desirable oligomeric compounds are produced by the enzymatic reactions.

In one or more embodiments, an enzyme based method for separating protein includes adjusting the volumetric productivity. Volumetric productivity is a critical factor in the process design as it defines the size of the reactor required for a designed output. Generally, volumetric productivity will be higher for a recycle method than for a fed batch or batch method. Thus, the volumetric productivity and type of method utilized might be optimized based on desired process conditions.

In one or more embodiments, an enzyme based method for separating protein includes adjusting the retention time. Retention time is defined as the average time that a material stays inside a specified space, such as a reaction vessel. Retention time can be mathematically defined as reactor volume divided by the total volumetric flow rate of all input (or output) streams). As should be appreciated from the above, for treating a constant volumetric flow of reactants, retention time is proportional to reactor volume. Thus, the use of shorter retention times generally means that smaller reactors can be used, saving capital and operating costs. But, a shorter retention time can also generally result in a less complete reaction. Thus, the retention time and reactor size utilized might also be optimized based on desired process conditions. In one or more embodiments, retention time is from 3 to 60 hours, in other embodiments, from 5 to 24 hours, in other embodiments, from 6 to 12 hours, and in other embodiments, from 12 to 24 hours.

In one or more embodiments, an enzyme based method for separating protein from protein-rich materials includes adjusting the particle size of the protein-rich material to achieve varying soluble carbohydrate concentrations. In one or more embodiments, the average particle size of a protein-rich material is from 15 µm to 100 µm, in other embodiments, from 20 µm to 90 µm, and in other embodiments, from 23 µm to 75 µm. In one or more embodiments, the average particle size of a protein-rich material is from 10 µm to 200 µm, in other embodiments, from 25 µm to 75 µm, and in other embodiments, from 35 µm to 60 µm. In one or more embodiments, the average particle size of a protein-rich material is 100 µm or less, in other embodiments, 75 µm or less, and in other embodiments, 50 µm or less. In one or more embodiments, the average particle size of a protein-rich material is 40 µm or less, in other embodiments, 30 µm or less, and in other embodiments, 25 µm or less.

In one or more embodiments, an enzyme based method for separating protein from protein-rich materials includes heating or toasting the protein-rich materials prior to the enzymatic hydrolysis. It is believed that the toasting and heat treatment increase the amount of protein that is collected in the protein concentrated product stream. That is, the toasting and heat treatment are believed to reduce the amount of protein that is in the product hydrolysate stream. The toasting or heat treatment is also believed to improve the carbohydrate hydrolysis into soluble carbohydrate and monosaccharides.

In one or more embodiments, a step of toasting or heating protein-rich materials is performed at a temperature of from 100° C. to 250° C., in other embodiments, from 150° C. to 200° C., and in other embodiments, from 160° C. to 180° C. In one or more embodiments, a step of toasting or heating protein-rich materials is performed at a time of from 5 min to 120 min, in other embodiments, from 30 min to 75 min, and in other embodiments, from 45 min to 60 min.

In one or more embodiments, a step of toasting or heating protein-rich materials increases the amount of protein that is collected in a protein concentrated product stream by 3 g/L or more, in other embodiments, 5 g/L or more, and in other embodiments, 7 g/L or more, when compared to a similar method that does not utilized a toasting or heating step. In one or more embodiments, a step of toasting or heating protein-rich materials increases the amount of protein that is collected in a protein concentrated product stream by 10 g/L or more, in other embodiments, 14 g/L or more, and in other embodiments, 16 g/L or more, when compared to a similar method that does not utilized a toasting or heating step.

In one or more embodiments, an enzyme based method for separating protein from protein-rich materials includes adjusting one or more parameters to improve the hydrolysis conversion to soluble carbohydrates, while also keeping the proteins intact and insoluble. Response surface methodology (RSM) can be used for modeling and analyzing the outcome of enzymatic hydrolysis by an enzyme broth. For example, reducing sugar and total carbohydrate conversions (%) can be used as the responses with pH, temperature, enzyme to protein-rich material ratio, and protein-rich material loading can be the independent variables. Each variable can be studied at five levels ($-\alpha$, $-1$, 0, 1, $+\alpha$), with the independent factors being used with a central composite design (CCD) approach.

The soluble carbohydrate conversion ($Y_{TC}$, %) and reducing sugar conversion ($Y_{RS}$, %) can be calculated as: $Y_{TC}=T_s/T_c\times100$ and $Y_{RS}=R_s/T_c\times100$, where $R_s$ and $T_s$ are concentrations of the soluble reducing sugar and total soluble carbohydrate, respectively, in the hydrolysate supernatant, and $T_c$ is the initial total carbohydrate (i.e. soluble and insoluble) concentration introduced with the protein-rich material. The influence of variables on the response can be analyzed using a multiple regression method with two quadratic polynomial equations. Analysis of variance can be conducted to evaluate the effects of variables and their interactions. Model coefficients can be analyzed for significance with insignificant terms being eliminated and the reduced model being adjusted. Response surface plots and the corresponding contour plots can then be constructed according to the developed models to visualize the variable-response relationship. The program Design-Expert 9 (Stat-Ease, Inc., Minneapolis, Minn.) can be used for the aforementioned regression analysis and for generating response surface plots.

In one or more embodiments, pH has quadratic effects on carbohydrate conversion, meaning that a lower than optimal pH gives lower conversion and a higher than optimal pH gives higher conversion. In one or more embodiments, a hydrolysis process is performed at an optimal pH, where optimal is defined as the pH that will give the highest carbohydrate conversion. In one or more embodiments, a hydrolysis process is performed at a pH of from 4.5 to 6.0, in other embodiments, from 4.7 to 5.2, and in other embodiments, from 4.8 to 5.2. In one or more embodiments, a hydrolysis process is performed at a pH of 4.7, or approximate thereto, in other embodiments, 4.8, or approximate thereto, in other embodiments, 5.1, or approximate thereto, and in other embodiments, 5.2, or approximate thereto.

In one or more embodiments, temperature has quadratic effects on carbohydrate conversion, meaning that a lower than optimal temperature gives lower conversion and a higher than optimal temperature gives higher conversion. In one or more embodiments, a hydrolysis process is performed at an optimal temperature, where optimal is defined as the temperature that will give the highest carbohydrate conversion. In one or more embodiments, a hydrolysis process is performed at a temperature of from 45° C. to 55° C., in other embodiments, from 47° C. to 53° C., and in other embodiments, 48° C. to 51° C.

In one or more embodiments, enzyme to protein-rich material ratio has a linear increasing effect on the carbohydrate conversion, meaning that increasing the enzyme to protein-rich material gives higher conversion, up to some threshold value. In one or more embodiments, a hydrolysis process is performed at an enzyme to protein-rich material ratio of 0.5 mL/g or approximate thereto, in other embodiments, 1 mL/g or approximate thereto, and in other embodiments, 2 mL/g or approximate thereto. In one or more embodiments, a hydrolysis process is performed at an enzyme to protein-rich material ratio of 3 mL/g or approximate thereto, in other embodiments, 4 mL/g or approximate thereto, and in other embodiments, 5 mL/g or approximate thereto. In one or more embodiments, a hydrolysis process is performed at an enzyme to protein-rich material ratio of from 0.5 mL/g to 5 mL/g, in other embodiments, from 1 mL/g to 4 mL/g, and in other embodiments, from 2 mL/g to 3 mL/g. In one or more embodiments, a hydrolysis process is performed at an enzyme to protein-rich material ratio of greater than 0.5 mL/g, in other embodiments, greater than 1 mL/g, and in other embodiments, greater than 2 mL/g.

In one or more embodiments, protein-rich material loading has a linear decreasing effect on carbohydrate conversion, meaning that increasing the protein-rich material loading gives lower conversion, up to some threshold value. In one or more embodiments, a hydrolysis process is performed at a protein-rich material loading of 100 g/L or approximate thereto, in other embodiments, 150 g/L or approximate thereto, and in other embodiments, 200 g/L or approximate thereto. In one or more embodiments, a hydrolysis process is performed at a protein-rich material of 250 g/L or approximate thereto, in other embodiments, 300 g/L or approximate thereto, and in other embodiments, 350 g/L or approximate thereto. In one or more embodiments, a hydrolysis process is performed at a protein-rich material of from 100 g/L to 350 g/L, in other embodiments, from 150 g/L to 300 g/L, and in other embodiments, from 200 g/L to 250 g/L. In one or more embodiments, a hydrolysis process is performed at a protein-rich material of less than 350 g/L, in other embodiments, less than 200 g/L, and in other embodiments, less than 150 g/L.

As disclosed in U.S. Ser. No. 14/400,076, incorporated by reference herein, a product stream from a hydrolysis process can include soluble saccharides and hydrolyzed carbohydrates (releasing sugars) that can be converted by fermentation to various valuable bioproducts. One or more embodiments of the present invention include a fermentation process resulting in improved fermentation productivity.

In one or more embodiments, a fermentation method includes controlling the pH of the fermentation composition. In one or more embodiments, a fermentation method includes gradually decreasing the pH of the fermentation composition over a length of time. In one or more embodiments, a fermentation method includes decreasing the pH of the fermentation composition at a substantially constant rate over a first length of time, maintaining the pH at a substantially constant pH for a second length of time, and decreasing the pH of the fermentation composition at a substantially constant rate for a third length of time. In one or more embodiments, the dissolved oxygen (DO) level is allowed to vary naturally (i.e. decrease when the cell respiration rate increases, and increase when the cell respiration rate decreases). In one or more embodiments, pure oxygen can be supplemented when necessary to maintain DO over 20% air saturation.

In one or more embodiments, a fermentation method includes decreasing the pH of the fermentation composition from 8 to 6, in other embodiments, from 7 to 5, and in other embodiments, from 7 to 6, over a first length of time. In one or more embodiments, a fermentation method includes a first length of time of from 1 day to 4 days, in other embodiments, from 1 day to 3 days, and in other embodiments, from 1 day to 2 days. In one or more embodiments, a fermentation method includes a first length of time of 1 day or approximate thereto, in other embodiments, 2 days or approximate thereto, and in other embodiments, 3 days or approximate thereto. In one or more embodiments, a fermentation method includes decreasing the pH of the fermentation composition at a rate of from 0.1 to 1.0 per day, in other embodiments, from 0.2 to 0.8 per day, and in other embodiments, from 0.1 to 0.4 per day, over a first length of time.

In one or more embodiments, a fermentation method includes a second length of time of from 1 day to 4 days, in other embodiments, from 1 day to 3 days, and in other embodiments, from 1 day to 2 days. In one or more embodiments, a fermentation method includes a second length of time of 1 day or approximate thereto, in other embodiments, 2 days or approximate thereto, and in other embodiments, 3 days or approximate thereto.

In one or more embodiments, a fermentation method includes decreasing the pH of the fermentation composition from 6 to 5, in other embodiments, from 6 to 4, and in other embodiments, from 5 to 4, over a third length of time. In one or more embodiments, a fermentation method includes a third length of time of from 1 day to 4 days, in other embodiments, from 1 day to 3 days, and in other embodiments, from 1 day to 2 days. In one or more embodiments, a fermentation method includes a third length of time of 1 day or approximate thereto, in other embodiments, 2 days or approximate thereto, and in other embodiments, 3 days or approximate thereto. In one or more embodiments, a fermentation method includes decreasing the pH of the fermentation composition at a rate of from 0.1 to 1.5 per day, in other embodiments, from 0.2 to 1.0 per day, and in other embodiments, from 0.1 to 0.5 per day, over a third length of time.

Without being bound by any theory, it is believed that the improved fermentation productivity resulting from a fermentation process is because the activity of hydrolytic enzyme depends on pH. The enzyme activity generally increases as pH is decreased from 7 (but above a threshold amount). The increased activity promotes faster generation of monomeric carbohydrates from the oligomeric and polymeric carbohydrates. However, if the monomeric carbohydrates are generated too fast, faster than the rate of microbial consumption, it may cause a negative effect on the enzyme production. This negative effect is a feedback regulation mechanism: when the monomeric carbohydrates are already present in a high enough concentration as food to the microbial cells, cells have lower or no incentive (induction) to produce more enzyme for generating more monomeric carbohydrates. The improved fermentation productivity with controlled pH decrease is thus believed to be due to better matching between the generation and consumption rates of the monomeric carbohydrates.

In one or more embodiments, a fermentation method includes controlling the dissolved oxygen (DO) level of a fermentation composition. In one or more embodiments, a fermentation method includes controlling the dissolved oxygen level of a fermentation composition at from 10% to 30%, in other embodiments, from 15% to 25%, and in other embodiments, from 18% to 22%. In one or more embodiments, a fermentation method includes controlling the dissolved oxygen level of a fermentation composition at 20% or approximate thereto. The dissolved oxygen level can be controlled as to guide the pH control such that the monomeric carbohydrate generation rate is sufficient to support the changing cell metabolic activity but not excessive as to cause negative effect on the induction for enzyme production. The dissolved oxygen level can be controlled by a control algorithm.

In light of the foregoing, it should be appreciated that the present invention significantly advances the art by providing one or more improved enzyme based methods of separating protein from protein-rich material. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof.

Fed Batch Examples 1-9

Examples 1 through 9 relate to example fed batch processes, particularly certain processes intended to increase the hydrolysis of soybean meal carbohydrate using an enzyme mixture produced by *Aspergillus niger* fermentation.

Materials and Equipment

Defatted soybean meal was provided by Archer Daniel Midland (Decatur, Ill.). Water used in the hydrolysis was Milli-Q water (18.2 MΩ-cm at 25° C.; Milli-Q Direct 8, Millipore S.A.S., Molsheim, France). $(NH_4)_2SO_4$ (granular), $KH_2PO_4$ (99% purity), HCl (concentrated acid, 37.4%) and NaOH (98.8%) were purchased from Fisher Scientific (Waltham, Mass.). Proteose peptone (from meat, Type I, for microbiology), $MgSO_4.7H_2O$ (99%), $MnSO_4.4H_2O$ (99%), $ZnSO_4.7H_2O$ (ACS reagent grade), $CoCl_2.6H_2O$, $FeSO_4.7H_2O$ (reagent grade), $CaCl_2.2H_2O$ (reagent grade), urea (98%), $NaN_3$ (>99%) and dinitrosalicylic acid (DNS, 98%) were purchased from Sigma-Aldrich (St. Louis, Mo.). *A. niger* (NRRL 341) seed culture was obtained from the United States Department of Agriculture (USDA) Agricultural Research Service (ARS) Culture Collection. Two 3 L Bioflo 110 fermentors (New Brunswick Scientific Co., Edison, N.J.) were used for enzyme production by fermentation. Absorbance was measured using a UV/Vis spectrophotometer (UV-1601, Shimadzu Corporation, Columbia, Md.). The hydrolysis experiments were conducted in a shaker (Thermo Scientific MaxQ 5000 Incubating/Refrigerating floor shaker, Ashville, N.C.). The centrifuge used was Sorvall Legend X1R from Thermo Scientific (Waltham, Mass.).

Enzyme Production

Enzyme mixture used was produced by the submerged fermentation of *A. niger* 341 strain. The fungal fermentation was performed in a 3 L fermentor containing 1 L of the following fresh medium: soy hulls, 20 g/L; proteose peptone, 1.4 g/L; $(NH_4)_2SO_4$, 4 g/L; $K_2HPO_4$, 0.32 g/L; $KH_2PO_4$, 0.21 g/L; and $MgSO_4.7H_2O$, 1 g/L. The initial pH was 6.7. Inoculation was done with a pre-grown culture at an initial cell concentration of about 0.1 g/L. Temperature and agitation were maintained at 23° C. and 350 rpm. The pH and DO (dissolved oxygen concentration) were allowed to vary naturally until they dropped to 6 and 20% (air saturation), respectively. Dissolved oxygen concentration (DO) was then maintained at 20% by automatic supplementation of pure oxygen as needed. pH was controlled at 6.0±0.1 by automatic addition of 1 M NaOH or HCl. The fermentation was stopped after 5 days when the enzyme production rate decreased significantly. The enzyme broth used for hydrolysis study was the cell- and solid-free supernatant collected by centrifugation of the fermentation broth at 8000 rpm (9000 g) for 10 min (Sorvall RC 5C, DuPont, Wilmington, Del.).

Fed Batch Hydrolysis

Two possible ways were demonstrated for improving the enzymatic processing effectiveness, particularly for processing reaction mixtures of high (total) soy meal concentrations, are to (1) add the enzyme in multiple batches along the processing and (2) add the enzyme and soy meal in multiple batches along the processing. Such operations involving multiple batch addition of materials into reactors are commonly termed as "fed-batch" operations. For the enzymatic processing, the fed-batch operation can be done in many different ways, divided in three groups: (1) the total amount of soy meal to be processed can be added in multiple batches at different times along the enzymatic processing, (2) the total enzyme can be added in multiple batches, and (3) both soy meal and enzyme can be added in multiple batches. All three groups were investigated in a series experiments. In these experiments the processing conditions such as temperature and pH were kept constant at 50° C. and 4.8, respectively. Total amounts of enzyme (10 ml) and soy meal (10 g) were also kept constant and the total liquid volume was fixed at 40 ml.

Hydrolysis by Recycling Hydrolysate

A first batch of enzymatic hydrolysis was done with 10 g soy meal in 10 ml enzyme and 30 ml water, i.e., at a total liquid volume of 40 ml and a soy meal concentration of 250 g/L. 30 ml supernatant was collected, by separation from the remaining solids (termed soy protein concentrate, SPC, in the field). A fraction of this separated supernatant was collected as hydrolysate and remaining fraction was recycled back for the next batch of hydrolysis of soy flour. Recycle rate was termed as percent of the starting liquid recycled in the next batch. Recycled liquid was supplemented with 10 ml of enzyme and additional deionized water to make up the total liquid volume 40 ml. Similar recycle scheme is followed for the following batches. Following N number of batches, the hydrolysis operation reaches a pseudo-steady state operation where the liquid hydrolysate collected and soy protein concentrate have similar compositions. For each batch the enzymatic processing conditions were kept the same: 50° C., pH 4.8, and desired batch processing time. Different batch processing time of 6, 8 or 12 hours were investigated.

Analytical Method

Sugar Analysis

The supernatants collected were analyzed for concentrations of reducing sugar and total carbohydrate. Reducing sugar concentration was measured with the dinitrosalicylic (DNS) acid method. This method is based on the principle that 3,5-dinitrosalicylic acid is reduced to 3-amino-5-nitrosalicylic acid in the presence of reducing sugar. The DNS reagent was prepared by dissolving 10 g 3,5-dinitrosalicylic acid, 16 g NaOH and 300 g sodium potassium tartrate (Rochelle salt) in 1 L deionized water. 3 ml DNS reagent and 1 ml supernatant sample were mixed in a test tube and then heated in a boiling water bath for 5 min. Deionized water was added to make the total volume in the tube 25 ml. After being cooled to the ambient temperature, the reacted mixture was measured for absorbance at 550 nm in the spectrophotometer. The reducing sugar concentration was then determined using the absorbance value according to a calibration curve established with standard glucose solutions. Total carbohydrate concentrations were measured using the phenol sulfuric acid colorimetric method. This method is based on the principle that carbohydrate reacts with sulfuric acid to produce furfural derivatives, which then react with phenol to develop a characteristic color. First, 1 mL sample was mixed with 1 ml aqueous phenol solution (5% v/v) in a test tube. 5 ml concentrated sulfuric acid was then added to the mixture. After 10 min reaction, the tube content was vortexed for 30 s and allowed to cool to room temperature. A reference solution was prepared in identical manner except that the 1 ml sample was replaced by deionized water. Then the absorbance at 490 nm was measured against the reference solution. The phenol used was redistilled and the 5% phenol solution was prepared fresh for each batch of analysis. Total carbohydrate concentration was determined from the absorbance reading according to a calibration curve obtained with standard glucose solutions, following the same procedure as described above.

Protein Content Analysis

The Kjeldahl method was used to measure the nitrogen contents of solid samples. The nitrogen content was multiplied by 6.25 to estimate the protein content. A 50 ml sample containing 10 to 200 mg/L protein was added to a flask and digested with 10 ml reagent containing 134 ml/1 concentrated sulfuric acid, 134 g/l potassium sulfate and 7.3 g/l cupric sulfate. The digestion was carried out to completion, until the reaction mixture became a clear solution. Then 30 ml water and 10 ml of a distillation reagent containing 500 g/l NaOH and 25 g/l $Na_2S_2O_3.5H_2O$ were added to the digested sample. This mixture was then distilled using a distillation unit (RapidStill 1, Labconco, Kansas city, MO) to produce ammonia gas, which was absorbed in a 0.1 N boric acid solution. Then the boric acid solution was titrated using a 0.1 N $H_2SO_4$. To find the nitrogen concentration in the sample.

Enzyme Activity Assay

Xylanase:

For best results, samples should be diluted to have xylanase activities in the range of 0.5-2 U/mL. The procedure was as follows: (1) Prepare 1 wt % substrate solution/suspension: mix 2 g beechwood xylan (Sigma Aldrich, St. Louis, Mo.) in 180 mL 0.05 M sodium citrate buffer (pH 5.3); heat the stirred mixture till the water vapor became apparent but not boiling; turn off heating and stir the mixture overnight; add 20 mL 0.05 M sodium citrate buffer (pH 5.3); and then store the substrate mixture at −20° C. for future use. (2) Add 100 µL test sample and 900 µL xylan substrate mixture to a 25 mL test tube. (3) Prepare the (enzyme-free) blank with only 900 µL xylan substrate. (4) Incubate the samples and blanks in a water bath at 50° C. for 5 min. (5) Add 3 mL regular DNS solution to each sample and blank to stop the enzyme reaction. And, add 100 µL test sample to the corresponding blank (to account for the potential turbidity introduced by the sample). DNS analysis was then done to determine the amount (mg) of reducing sugar released, using D-xylose solutions as standards. Calculate the xylanase activity by the following equation:

$$\text{Xylanase}\left(\frac{U}{mL}\right) = \frac{\text{xylose released (mg)}}{(5 \text{ min})(0.1 \text{ mL enzyme sample})} \times$$
$$\frac{1 \text{ mmol}}{150.13 \text{ mg}} \times \frac{1000 \text{ µmol}}{1 \text{ mmol}}$$
$$= 13.32 \times \text{xylose released (mg)}.$$

Pectinase:

A method was developed using assay condition of pH 4.8 and 50° C. Samples should be diluted to the suitable enzyme activity range of 0.3-0.7 U/mL. The procedure was similar to that described above for the xylanase assay, with four differences. First, the substrate solution/suspension was prepared by mixing 0.5 g polygalacturonic acid (Sigma Aldrich, St. Louis, Mo.) in 100 mL 0.1 M sodium citrate buffer and then adjusting the pH to 4.8. Second, the samples and blanks were incubated at 50° C. for 30 min (instead of 5 min as in the xylanase assay). Third, the DNS solution used did not contain sodium-potassium tartrate to prevent precipitation of residual substrate. Fourth, the calibration for determining the released amount of reaction product(s) is made with standard solutions of D-galacturonic acid (monohydrate). The polygalacturonase activity was calculated according to the following equation:

$$\text{Polygalacturonase}\left(\frac{U}{mL}\right) = 1.57 \times \text{galacturonic acid released (mg)}$$

The pectinase assay was the same as that for polygalacturonase activity except that the substrate solution was prepared with citrus pectin (Sigma Aldrich, St. Louis, Mo.). Also, heating was necessary to prepare more homogeneous solution/suspension of the pectin substrate in citrate buffer.

α-Galactosidase:

The procedure was as follows: (1) prepare the substrate solution by dissolving 0.033 g p-nitrophenyl-α-D-galactopyranoside (Sigma Aldrich, St. Louis, Mo.) in 100 mL 0.1 M sodium citrate buffer (pH 4.8); (2) mix 100 µL test sample with 900 µL substrate solution; (3) prepare the (enzyme-free) blank with only 900 µL substrate solution; (4) incubate samples and blanks at 50° C. for 10 min; (5) add 2 mL 0.5 M sodium carbonate (pH 9.8) to each sample and blank to stop the reaction and develop the color from released p-nitrophenol; (6) add 100 µL test sample to the blank; and (7) measure the absorbance at 405 nm. Test samples should be diluted to have α-galactosidase activities of 0.05-0.2 U/mL. Calibration established with pure p-nitrophenol standards was used for quantitation of the enzyme-released p-nitrophenol. α-Galactosidase activity was calculated by the following equation:

$$\alpha - \text{Galactosidase}\left(\frac{U}{mL}\right) = 7.19 \times p - \text{nitrophenol released (mg)}.$$

Example 1—Fed Batch Soy Example

Figure 5:
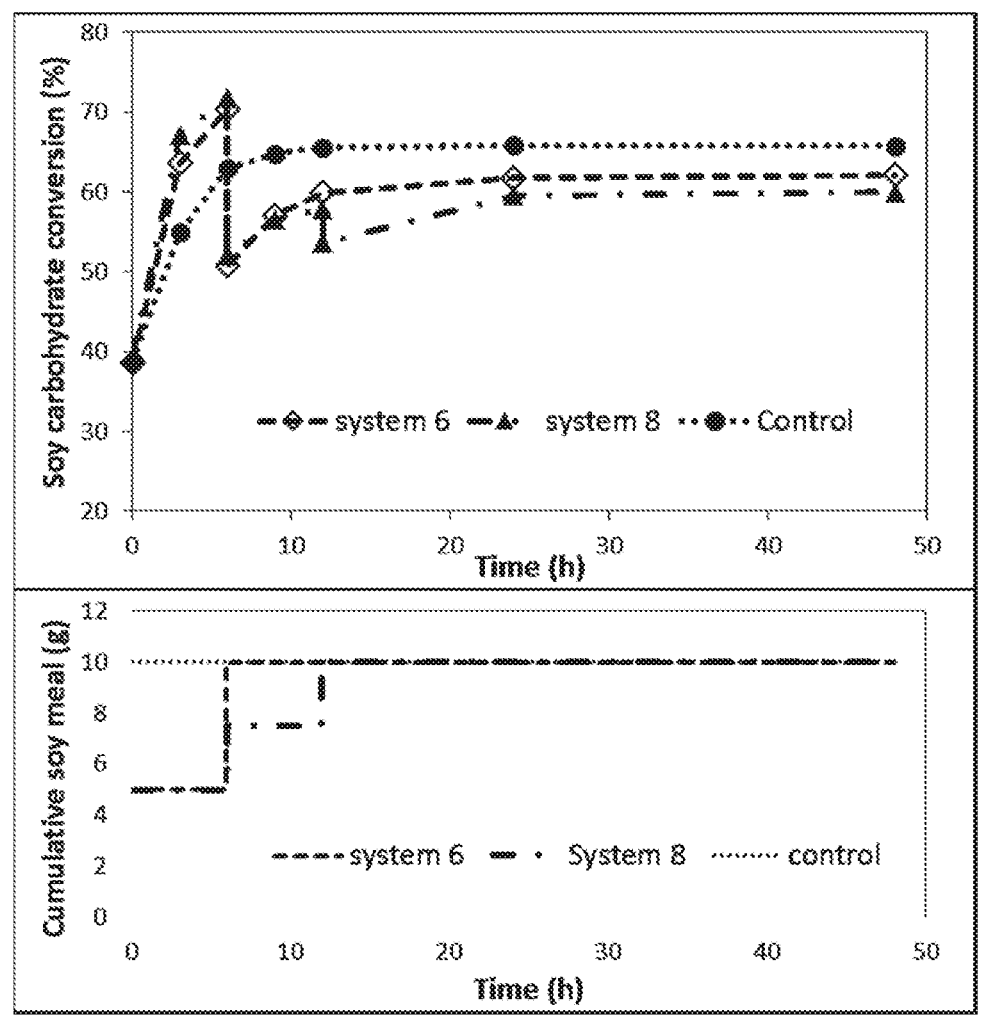
FIG. 5 is a graph showing an example of the effect of fed batch addition of soy meal on conversion of carbohydrate in soy meal to soluble carbohydrate in the hydrolysate.

In this group, soy meal was added in multiple batches while the entire enzyme amount was added at the beginning of the enzymatic processing in a single batch. The multiple additions of soy meal are indicated in FIG. 5, together with the comparison of soy carbohydrate conversions achieved by different addition schemes.

The results showed that the enzymatic processing performance was poorer when the soy meal was added in multiple batches. Even though the initial rates of hydrolysis were higher in the systems with fed batch addition of soy meal, the conversions were significantly lower after the second and third batches of soy meal were added. The results also suggested that the activity of the enzyme added at the beginning of enzymatic processing has become lower over time, prior to the second and third batches of soy meal addition. This enzyme activity decrease with time was presumably due to deactivation at the processing conditions (50° C. and pH 4.8) or irreversible binding of the enzyme to non-substrate solids. This could cause the lower hydrolysis rates observed after the second and third batches of soy meal addition.

Example 2—Fed Batch Enzyme Example

Figure 6:
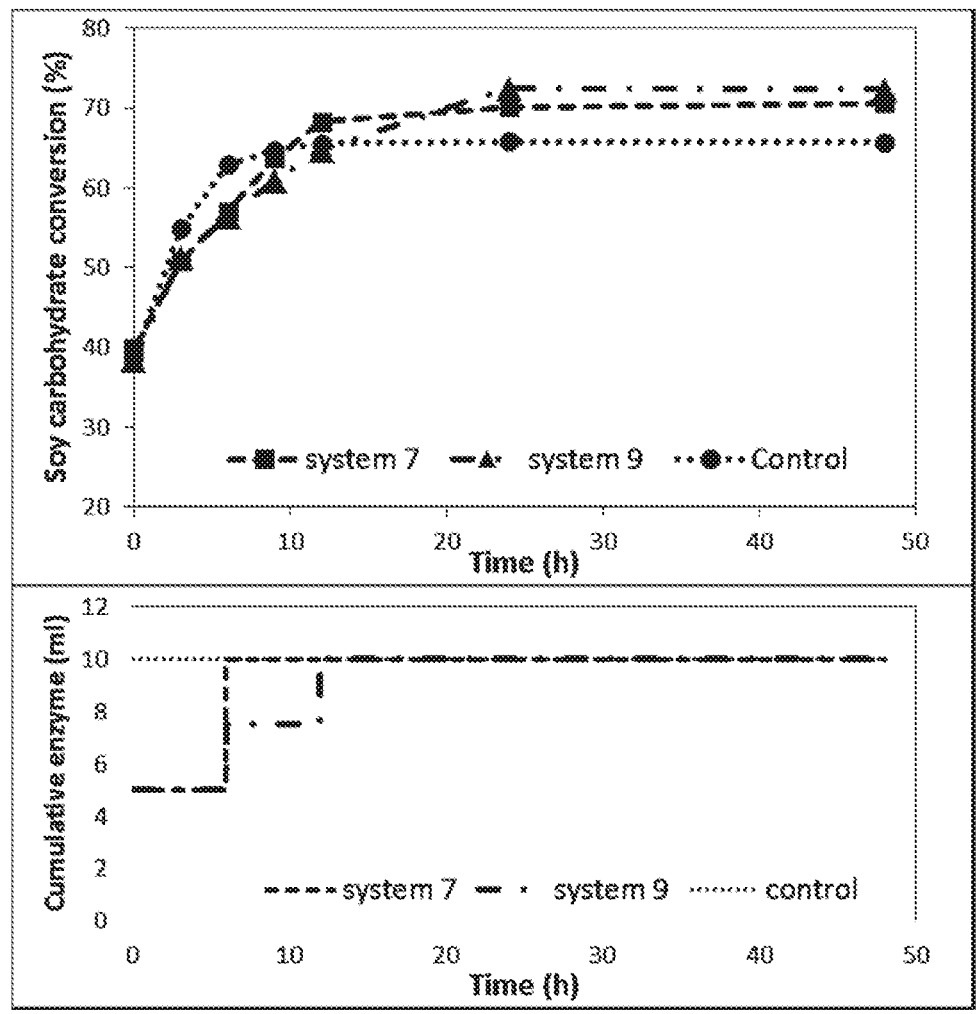
FIG. 6 is a graph showing an example of the effect of fed batch addition of enzyme on the conversion of carbohydrate in soy meal to soluble carbohydrate in the hydrolysate.

When enzymes were added in batches and soy meal was added initially in a single batch, the final hydrolysis yield was found to be improved over the control (simple batch), as shown FIG. 6. Initially the hydrolysis rates in the fed-batch enzyme addition systems were lower than that in the control (because the control had a higher enzyme-to-soy meal ratio). After the addition of the second and third batches of enzyme, the conversion increased to levels higher than that in the control system.

Example 3—Fed Batch Soy and Enzyme Example

Figure 7:
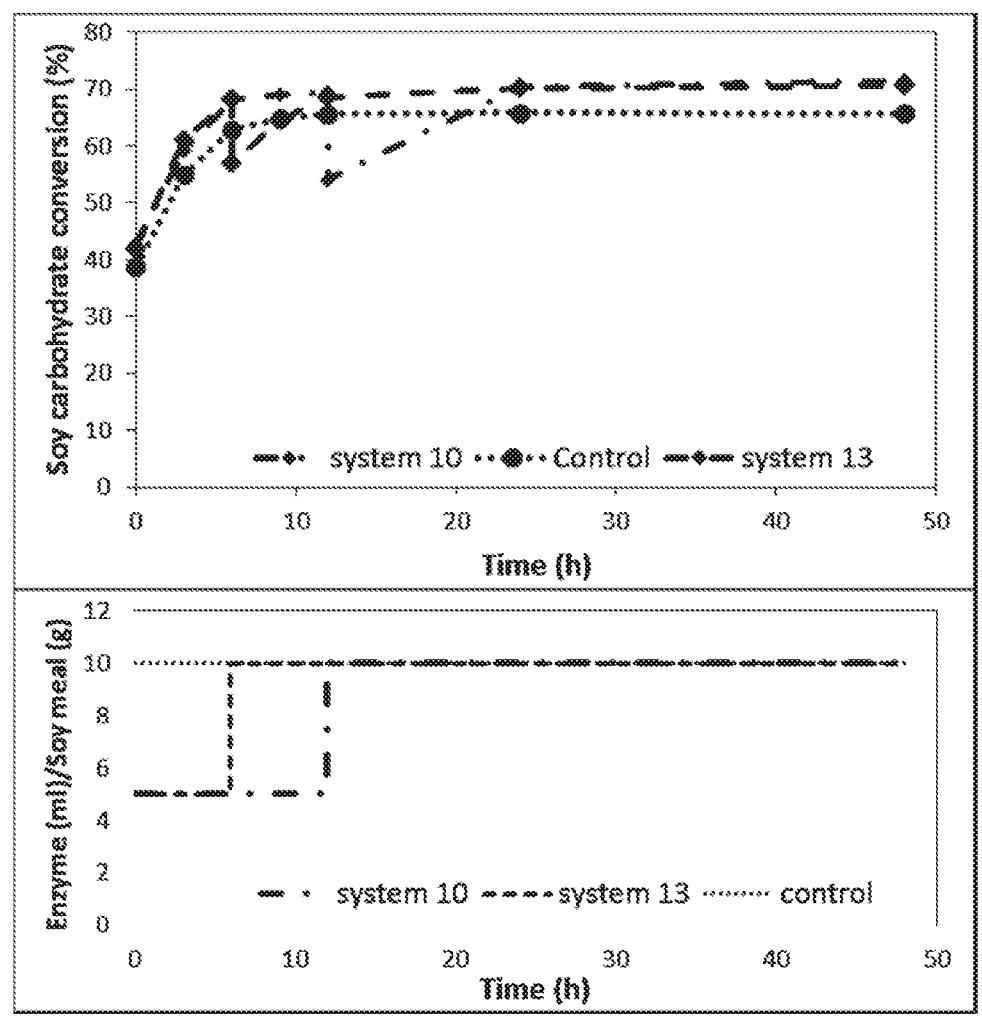
FIG. 7 is a graph showing an example of the effect of fed batch addition of both enzyme and soy meal, simultaneously, on the conversion of carbohydrate in soy meal to soluble carbohydrate in the hydrolysate.

When soy meal and enzyme were added simultaneously in multiple batches (FIG. 7), the carbohydrate conversion was higher than the control systems.

In comparison, using fed-batch enzyme addition (to soy meal at a concentration of 250 g/L), the soy carbohydrate conversion was increased from 65% in control to 72%; using fed-batch addition of enzyme and soy meal simultaneously (to a final soy meal concentration of 250 g/L), the conversion was increased to 71%.

Comparative Example 1—Fed Batch Control Batch Example

Batch Hydrolysis

Enzymatic hydrolysis was conducted in 250 ml flasks in a shaking incubator at 50° C. and 250 rpm. Flask contained 40 ml enzyme broth and an amount of soybean meal depending on the designed substrate concentration. Dispersed soybean meal in deionized water was warmed to 50° C. 1 M hydrochloric acid was used to initially adjust the pH to 4.8. 0.5% sodium azide was added to prevent from microbial contamination. Enzyme broth was then added to the dispersed soybean meal solution. During hydrolysis pH was checked every 4 h and adjusted to 4.8 with 1 M NaOH if required; pH had a slight tendency to decrease during the hydrolysis. Samples were taken at regular intervals in triplicate and heated immediately for 10 min in boiling water to deactivate the enzymes. Samples were then centrifuged to separately collect the solids and supernatant for further analysis. The control results are disclosed elsewhere herein.

Example 4

Figure 8:
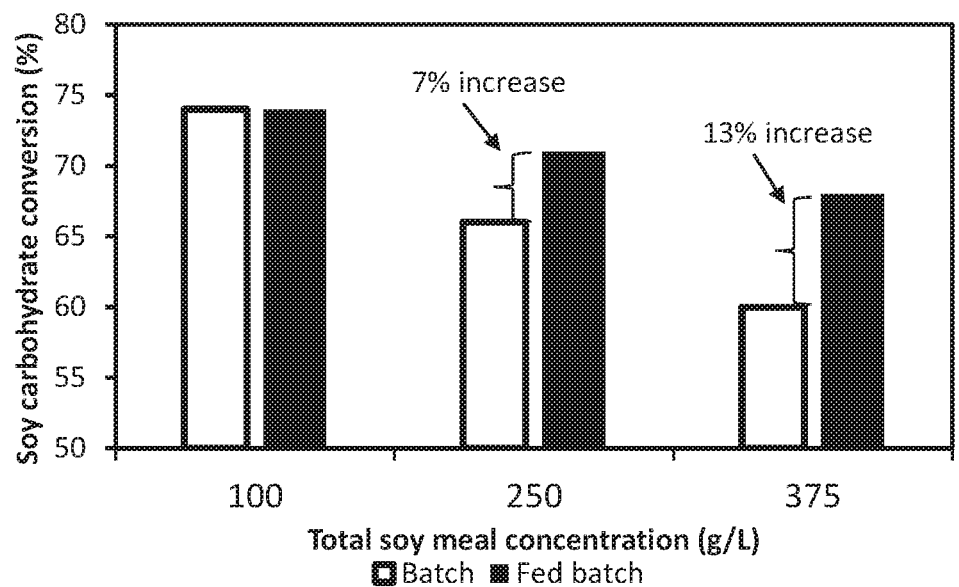
FIG. 8 is a graph showing an example of the comparisons of final soy carbohydrate conversion achieved by batch versus fed-batch (with both enzyme and soy meal) addition for different total soy meal concentrations.

Simultaneous fed-batch addition of soy meal and enzyme was found to be particularly beneficial for processing soy meal at cumulative (total) concentrations higher than 250 g/L. This is shown in an additional experiment where this fed-batch addition approach of both enzyme and soy meal was applied to different cumulative soy meal concentrations, from 100 g/L to 375 g/L. Compared in FIG. 8 are the carbohydrate conversions achieved by the batch process and the fed-batch addition of both enzyme and soy meal at different final soy meal concentrations. The % improvement in carbohydrate conversion by the fed-batch operation is larger for the system with a higher soy meal concentration. More importantly, the negative effect of high solid loading can be substantially mitigated by the fed-batch operation.

Example 5

In the above examples without recycle, the maximum soluble carbohydrate concentration (measured by the common reducing sugar analysis) achievable was 65-70 g/L from processing a total of 375 g/L soy meal. To further increase the sugar concentration in the hydrolysate the recycle of the enzyme was investigated. For designing the recycle process enzyme degradation for pectinase and α-galactosidase over time in the batch process was investigated. Pectinase activity was mostly removed from the hydrolysate after 6 h (although a portion could be adsorbed on the solid substrate and continue act on the soy meal). The longer hydrolysis time helped to achieve degradation of soluble carbohydrate to reducing sugars. It was therefore thought that longer batch processing time was likely to have lower marginal benefit. So the recycle study was conducted to achieve additional benefit in the process. The effect of recycle rate, retention time, and enzyme loading effects during the recycle process were further investigated.

Example 6

With the progression of recycle, sugar concentration in the liquid builds up. The development in the sugar concentration depends on the sugar conversion after each hydrolysis, the efficiency of the solid liquid separation and the rate of liquid hydrolysate recycle. For a simplified calculation, the sugar concentration build up can be represented by the geometrical series. The below equations can be used for prediction of experimental results at different recycle rate.

$$S_n = S_0 + S_0 r + S_0 r^2 + S_0 r^3 + \ldots + S_0 r^n$$

$$S_n = S_0 \left(\frac{1 - r^{n+1}}{1 - r}\right)$$

$$S_{max} = S_0 \left(\frac{1}{1 - r}\right)$$

Where $S_n$ is the sugar concentration of the hydrolysate after nth recycle, r is the recycle rate and $S_0$ is the sugar concentration of the hydrolysate after without any recycle. $S_{max}$ represents the maximum sugar concentration achievable using a specific recycle rate, which will no longer increase with more recycle step.

Total soluble carbohydrate and reducing sugar concentration and activity of α-galactosidase progression along with each recycle of hydrolysate was found. The enzyme activity used in this process was cellulase 0.7 FPU, xylanase 180 U, pectinase 7.25 U and α-galactosidase of 8.1 U per g of soybean flour. The recycle rate of 62.5% of the starting liquid and retention time of 8 hours for every batch were used in the recycle process. After 7 recycle systems, a sugar concentration of 104.28 g/L was achieved which is comparable to the predicted concentration of 107 g/L achievable by the equation. This suggests that there was no product inhibition at this high concentration of hydrolyzed sugar. It was found that in the first batch before recycle the reducing sugar concentration was only 27 g/L compared to the total carbohydrate concentration of 40 g/L. Reducing sugar concentration was lower because the retention time was only 8 hours and the α-galactosidase present in the enzyme broth was not capable to degrade all the soluble carbohydrate, mainly stachyose and raffinose, into monomer. However, the galactosidase activity is increased when it would be recycled in the following batch. The build-up of α-galactosidase activity helped to degrade the soluble carbohydrate to reducing sugar over progression of recycle process. After 5 recycle steps, the total carbohydrate and reducing sugar concentration became almost same. The increase of α-galactosidase activity to approximately 15.9 U/g of soy flour helped to neutralize the difference between total carbohydrate and reducing sugar. This indicates the benefit of using recycle process to degrade the total carbohydrate in the reducing sugar by building up the activity over recycle process within very short retention time.

Example 7

Different enzyme loadings in the recycle process were studied to understand the effect on the effective conversion of the total soluble carbohydrate to reducing sugars as hydrolysate value is higher with soluble sugars in the monomeric form. Total soluble carbohydrate and reducing sugar concentration with the progression of recycle process using three different strength of enzyme was found. Enzyme strength was designated as low medium and high strength. The total soluble carbohydrate concentration was comparable with all three strength of enzyme. With high strength enzyme the maximum concentration, 109 g/l, was slightly higher than that with the low and medium strength enzyme. However, the reducing sugar concentration differed significantly with the strength of enzymes. With the high strength enzyme, the reducing sugar concentration and total carbohydrate concentrations are almost similar from the very first batch of the recycle system. On the other hand, with low strength enzyme, the gap between total carbohydrate and the reducing sugars widens during the first 3 recycle steps, then the gap started to reduce in the subsequent recycles. This indicates that with low enzyme strength, the difference initially was due to low α-galactosidase activity which was insufficient to breakdown the soluble carbohydrates, mainly oligosaccharides e.g. stachyose and raffinose, to reducing sugars. However, with the progression of the recycle, the α-galactosidase activity build up and after 4 recycle steps the increased α-galactosidase activity were able to close the difference between the soluble carbohydrates and reducing sugars. Using weaker enzyme strength, the total soluble carbohydrate and reducing sugar was not the same at steady state condition but with medium strength enzyme it was able to degrade all the soluble carbohydrate in reducing sugar in steady state. This suggests that if low enzyme strength is used then to reach degrade the total soluble carbohydrate to reducing sugar, longer retention time may be required.

Example 8

The effect of the proportion of recycled hydrolysate was studied by comparing the recycle rate of 25%, 37.5%, 50% and 62.5% in hydrolysis. The maximum sugar concentration (total carbohydrate) achieved and the corresponding protein content in the soy protein precipitate was determined. The retention time was considered for 8 hours and the enzyme used with the activity of cellulase 0.7 FPU, xylanase 180 U, pectinase 7.25 U and α-galactosidase of 8.1 U per g of soybean flour. Highest sugar concentration achieved was 104 g/l using highest recycle rate of 62.5%. The maximum sugar concentration for other recycle rate decreased along with the decreasing recycle rate. At lowest recycle rate of 25%, the sugar concentration achieved was only 54 g/l. Higher sugar concentration is expected for higher value of hydrolysate, but it came at the expense of the protein content decrease in the soy protein concentrate. The protein content can be decreased to as low as 58% in the highest recycle rate of 62.5%. In the lower recycle rate of 25%, the protein content is 66% compared to 69% in the batch process. The protein content decreased due to two factors. One is due to the trapped hydrolysate with high sugar concentration inside the wet protein. As the soluble carbohydrate concentration in hydrolysate increased with hydrolysate recycle, the amount of carbohydrate trapped in the wet solid mass also increased. Another reason is the lower retention time of the solids compared to batch process, which is responsible for not hydrolyzing the insoluble carbohydrates in the solid effectively. However, remaining hydrolyzed reducing sugar in the protein concentrate may be beneficial for its use as animal and aquaculture feed because the monosaccharides can serve as readily available energy source to the animals and fish without indigestion problem. But, it reduces the protein content in the concentrate. However, the protein content can be further increased by using a wash step to remove the soluble carbohydrate to increase the protein content. Whether the wash step to increase the protein content is required or not, it will depend on the protein requirement of the specific use of the soy protein concentrate.

Example 9

Volumetric productivity is a critical factor in the process design as it defines the size of the reactor required for a designed output. The volumetric productivity of the different hydrolysis strategies discussed in the current study was studied. The volumetric productivity of sugars and protein concentrates were compared among batch, fed-batch and recycle process. In recycle process, volumetric productivity of both the sugar in the hydrolysate, 3.75 $gl^{-1}h^{-1}$, and protein, 10.25 g $kg^{-1}h^{-1}$, were significantly higher compared to the batch and fed batch hydrolysis. In a batch reaction, the total amount of liquid is inefficiently incubated with fixed amount of substrate throughout the complete reaction time, while in recycle process same amount of liquid is more effectively utilized for saccharification of multiple addition of solid substrate. The amount of water usage is also decreased significantly in recycle process. Sometimes viscosity of the liquid due to high solid loading can be inhibitory for the hydrolysis. To circumvent the high viscosity stage, gradual feeding of the substrate has been studied in the fed batch process. But in fed batch process the total solid to liquid ratio was kept constant which didn't increase the volumetric productivity. But in recycle process, the fresh substrate was added after separating solids from the previous loading and therefore a lower viscosity can be maintained even after new addition of substrate.

Retention time of the solids in the recycle process is also an important factor in terms of volumetric productivity. Volumetric productivity of sugars and protein concentrate with different retention time of solids in the recycle process were determined. Higher productivity was obtained for both sugars and protein concentrate with lower retention time. However, the lower retention time is responsible for lower protein content in the soy protein concentrate as discussed earlier. So the decision on the right retention time will depend on the protein content requirement in the soy protein concentrate product for the specific use.

Example 10

An empirical kinetic model for the hydrolysis of soy flour carbohydrate using fungal enzyme mixtures containing various cellulase, xylanase, pectinase and α-galactosidase activities and soy flour concentrations was developed.

Materials and Equipment

Defatted soy flour (7B soy flour) and soy hulls were provided by Archer Daniel Midland (Decatur, Ill.). Water used in the hydrolysis was Milli-Q water (18.2 MΩ-cm at 25° C.; Milli-Q Direct 8, Millipore S.A.S., Molsheim, France). $(NH_4)_2SO_4$ (granular), $KH_2PO_4$ (99% purity), HCl (concentrated acid, 37.4%) and NaOH (98.8%) were purchased from Fisher Scientific (Waltham, Mass.). Proteose peptone (from meat, Type I, for microbiology), $MgSO_4.7H_2O$ (99%), $MnSO_4.4H_2O$ (99%), $ZnSO_4.7H_2O$ (ACS reagent grade), $CoCl_2.6H_2O$, $FeSO_4.7H_2O$ (reagent grade), $CaCl_2.2H_2O$ (reagent grade), urea (98%), $NaN_3$ (>99%) and dinitrosalicylic acid (DNS, 98%) were purchased from Sigma-Aldrich (St. Louis, Mo.). *A. niger* (NRRL 341), *A. aculeatus* (NRRL 2053), and *T. reesei* Rut-C30 (NRRL 3469) seed cultures were obtained from the United States Department of Agriculture (USDA) Agricultural Research Service (ARS) Culture Collection. Two 3 L Bioflo 110 fermentors (New Brunswick Scientific Co., Edison, N.J.) were used for enzyme production by fermentation. Absorbance was measured using a UV/Vis spectrophotometer (UV-1601, Shimadzu Corporation, Columbia, Md.). The hydrolysis experiments were conducted in a shaker (Thermo Scientific MaxQ 5000 Incubating/Refrigerating floor shaker, Ashville, N.C.). The centrifuge used was Sorvall Legend X1R from Thermo Scientific (Waltham, Mass.).

Enzymes

Commercial cellulase Spezyme CP (Dupont, Cedar Rapids, Iowa) and pectinase (Sigma-Aldrich, St. Louis, Mo.) were used in addition to the enzyme broths produced in the laboratory. Three different fungal species, *A. niger* (NRRL 341), *A. aculeatus* (NRRL 2053) and *T. reesei* Rut C-30 (NRRL 3469), were used to produce the enzyme broths. The fungal fermentation was performed in a 3 L fermentor containing 1 L of the following fresh medium: soy hulls, 20 g/L; proteose peptone, 1.4 g/L; $(NH_4)_2SO_4$, 4 g/L; $K_2HPO_4$, 0.32 g/L; $KH_2PO_4$, 0.21 g/L; and $MgSO_4.7H_2O$, 1 g/L. The initial pH was 6.7. Inoculation was done with a pre-grown culture at an initial cell concentration of about 0.1 g/L. Temperature and agitation were maintained at 23° C. and 350 rpm. The pH and DO (dissolved oxygen concentration) were allowed to vary naturally until they dropped to 6 and 20% (air saturation), respectively. Dissolved oxygen concentration (DO) was then maintained at 20% by automatic supplementation of pure oxygen as needed. pH was controlled at 6.0±0.1 by automatic addition of 1 M NaOH or HCl. The fermentation was stopped after 5 days when the enzyme production rate decreased significantly. The enzyme broth used for hydrolysis study was the cell- and solid-free supernatant collected by centrifugation of the fermentation broth at 8000 rpm (9000 g) for 10 min (Sorvall RC 5C, DuPont, Wilmington, Del.).

Enzymatic Hydrolysis

Enzymatic hydrolysis was conducted in 250 ml flasks in a shaking incubator at 50° C. and 250 rpm. Each flask contained 40 ml enzyme broth and an amount of soy flour depending on the designed substrate concentration. Two duplicate control systems, prepared with enzyme-free deionized water, were included in each batch of experiments. Dispersed soy flour in deionized water was warmed to 50° C. Enzyme broth and then deionized water was added. 1 M hydrochloric acid was used to initially adjust the pH to 4.8. During hydrolysis pH was checked every 4 h and adjusted to 4.8 with 1 M NaOH if required; pH had a slight tendency to decrease during the hydrolysis. Samples were taken at 0, 4, 8, 16, 22 and 48 h in triplicate and heated immediately for 10 min in boiling water to deactivate the enzymes. Samples were then centrifuged to separately collect the solids and supernatant. Supernatants were analyzed for concentrations of reducing sugars and total carbohydrate (methods described in the next section). Total carbohydrate and reducing sugar contents in the soy flour used were separately measured. The total carbohydrate conversion achieved was calculated by dividing the total soluble carbohydrate found in the solution by the total carbohydrate present in the soy flour initially added. The reducing sugar conversion achieved was determined similarly.

Analytical Methods

Cellulase, xylanase and pectinase activities were measured according to generally known methods. A reported assay was used to measure the activity of α-galactosidase. Reducing sugar concentrations in the hydrolysates were measured by the dinitrosalicylic (DNS) acid method. DNS solution (3 ml) was placed in a test tube and mixed with 1 ml sample. Then the mixture was heated in a boiling water bath for 5 min. The tube was added with water to 25 ml total volume and cooled to ambient temperature. Absorbance was then measured at 550 nm with a spectrophotometer. The absorbance was converted to reducing sugar concentration according to the calibration curve obtained with glucose solutions as standards. Total carbohydrate concentrations were measured by the phenol-sulfuric acid colorimetric method. A 1 ml sample was mixed with 1 ml aqueous phenol solution (5% w/w) in a test tube, followed by addition of 5 ml concentrated sulfuric acid. 5% phenol in water (w/w) was prepared immediately before the analysis. After 10 min reaction without mixing, the mixture was vortexed for 30 s, cooled to room temperature, and then measured for the absorbance at 490 nm. Blanks were prepared in the identical manner with 1 ml deionized water. Total carbohydrate and reducing sugar contents in the soy flour were determined by first processing the soy flour according to the NREL method and then analyzing the acid hydrolysate by the phenol-sulfuric acid colorimetric method and dinitrosalicylic acid (DNS) method.

Experimental Design

The overall procedure followed included: (1) running many hydrolysis experiments using different enzyme mixtures, soy flour (SF) concentrations, and enzyme-to-SF ratios; (2) fitting all final conversion results to an enzyme saturation-type model to determine the maximum conversions attainable from individual carbohydrate type (hypothetically grouped into pectin, xylan, cellulose, and oligosaccharides) by the corresponding enzyme activity used (pectinase, xylanase, cellulase, and α-galactosidase) and to obtain the best-fit model parameters; and (3) fitting the conversions attained at different hydrolysis time to a kinetic (time-dependent) model that builds on the model parameters obtained from Step (2). The number of hydrolysis experiments made and the ranges of factors varied in the experiments are summarized in Table 1.

TABLE 1

The number of hydrolysis experiments made and the ranges of factors varied in the experiments, for fitting the conversions attained to the two models.

| Enzyme mixture source | No. of systems | Cellulase (FPU/g) | Xylanase (U/g) | Pectinase (U/g) | α-galactosidase (U/g) | Soy meal loading (g/L) |
|---|---|---|---|---|---|---|
| *A. niger* | 32 | 0.04-2 | 9.5-456 | 0.4-19.2 | 0.5-22 | 50, 100, 125, 200, 250 |
| *T. reesei* | 24 | 0.2-2.0 | 4-191 | 0.03-1.37 | 0.01-0.32 | 100, 150, 250 |
| *A. aculeatus* | 8 | 0.35-1.2 | 14-119 | 2.6-13.3 | 0.5-3.6 | 150, 250 |
| *A. niger* + *T. reesei* | 20 | 0.5-20.7 | 19.3-618.2 | 1.72-50 | 2.45-59.3 | 100, 200, 250 |
| Commercial cellulase | 4 | 2.0-30 | 17.5-122 | 0.12-1.6 | 0.05-0.75 | 250 |
| Commercial pectinase | 4 | 0.4-2.05 | 3.5-18.0 | 24-120 | 0.5-2.6 | 250 |
| Commercial cellulase + *A. niger* | 6 | 2.5-29.5 | 70-190 | 1.4-6.5 | 0.44-8.2 | 250 |
| Commercial pectinase + *T. reesei* | 6 | 0.5-2.5 | 10.5-112.2 | 14.5-60.2 | 0.4-1.9 | 250 |

Modeling for Maximum Contributions from Different Hydrolytic Enzyme Groups

A saturation-type model was used to describe the final conversions achieved after 48 h hydrolysis at the optimized reaction conditions (pH 4.8, temperature 50° C.). Conversions to two categories of soluble carbohydrate in the hydrolysate were determined: total carbohydrate and reducing sugars. Choice of the final condition was based on the hydrolysis profile when the total carbohydrate and reducing sugar concentrations no longer increase. Accordingly, 48 h was selected as the final conversion time. The total carbohydrate conversion was calculated by dividing the total soluble carbohydrate found in the hydrolysate by the total carbohydrate present in the soy flour initially added. The soluble carbohydrate found in the hydrolysate include (1) the oligomeric and monomeric carbohydrates that are already water soluble without enzymatic hydrolysis and (2) those that become soluble by the enzymatic degradation of originally insoluble carbohydrate. Accordingly, total carbohydrate conversion was expressed by the summation of four portions: originally soluble carbohydrate and the 3 portions solubilized due to hydrolysis by individual enzymes (cellulase, xylanase, and pectinase), as shown in the above Formula (1).

For modeling the reducing sugar conversion ($X_{RS}$), the soluble total carbohydrate portion ($\alpha_o$) was divided into 2 portions: soluble monosaccharides ($\alpha_{Ors}$) and the α-galactosidase generated reducing sugars ($\alpha_g$), and the above Formula (2) was utilized.

The above Formulas (3)-(5) were then used to model kinetic (i.e. time-dependent) hydrolysis performance. During model fitting, the conversion from each term was limited by the maximum fraction of contribution ($\alpha_c, \alpha_x, \alpha_p, \alpha_g$) of that enzyme group, as obtained from Formulas (1) and (2).

Hydrolysis Profiles

Some profiles depicting the release over time of soluble carbohydrate from solid soy flour substrate into the liquid hydrolysate were found. The released soluble carbohydrate was measured respectively as total carbohydrate and reducing sugars. Different concentrations of an enzyme broth was found to affect the hydrolysis. The broth was produced by *A. niger* and was measured to have the following activities: 0.5 FPU/ml cellulase, 171 U/ml xylanase, 5.5 U/ml pectinase and 7.1 U/ml α-galactosidase. The broth was diluted to different strengths with dilution factors of 1 (undiluted), 2, 4 and 10. The conversions were lower and slower with increasing dilution factors. For examples, the undiluted broth gave maximally 80% conversions to both total carbohydrate and reducing sugars while the 10-fold diluted broth yielded only 45% reducing sugar conversion and 54% total carbohydrate conversion. Hydrolysis rates were also different. Total carbohydrate conversion increased significantly faster than the reducing sugar conversion. With the undiluted broth, total carbohydrate conversion reached the maximum level (80%) after about 10 h but the reducing sugar conversion increased slower and reached the same maximum level at the end of experiment (48 h). With diluter enzyme broths, both conversions increased slower. Total carbohydrate analysis does not differentiate between oligomeric and monomeric carbohydrates but the reducing sugar conversion increases with increasing degrees of monomerization. The same total carbohydrate and reducing sugar conversions achieved, after 48 h reaction, by the undiluted broth suggested all carbohydrates in that hydrolysate were monomers. The lower reducing sugar conversions and their slower increasing rates, compared to total carbohydrate conversions, suggested that hydrolysis of oligomeric carbohydrates in the hydrolysate was rate-limiting and that the enzyme broth used had a suboptimal composition of enzyme activities.

The effects of substrate concentration (solid loading) on the total carbohydrate and reducing sugar conversions were also determined. The increase in solid concentration has clearly negative effects on the conversions. Compared at 48 h the total carbohydrate conversion dropped from 68% to 59% and the reducing sugar conversion dropped from 63% to 56% due to the increase of soy flour concentration from 50 to 200 g/L. Such an adverse effect of increasing solid substrate concentration on enzymatic hydrolysis confirmed the need to incorporate the substrate concentration effect in the kinetic modeling formulas.

Modeling for Maximum Contributions from Different Hydrolytic Enzyme Groups

Table 2 shows the determined parameters for Formulas (1) and (2). These equations describe well the experimentally measured reducing sugar and total carbohydrate conversions (after 48 h reaction).

TABLE 2

Exemplary best-fit model parameters for Formula 1 and Formula 2, which give the maximum fractions of contribution ($\alpha$) and half-maximum enzyme loading constants (k) for different substrate-enzyme groups.

| Maximum fractions of contribution | | Half-maximum constants (U/g SF) | |
|---|---|---|---|
| $\alpha_{0rs}$ | 0.078 | — | — |
| $\alpha_g$ | 0.278 | $K_g$ | 1.16 |
| $\alpha_c$ | 0.043 | $K_c$ | 27.5 |
| $\alpha_x$ | 0.282 | $K_x$ | 3.15 |
| $\alpha_p$ | 0.318 | $K_p$ | 14.7 |

According to the modeling results shown in Table 2, about 8% of the soy carbohydrate was readily measurable as soluble reducing sugars in the hydrolysate ($\alpha_{0rs}$). Another 27% ($\alpha_g$) were also measured as soluble carbohydrate (by the phenol-sulfuric acid based analysis) but would be measured as reducing sugars only after the enzymatic hydrolysis by $\alpha$-galactosidase (and sucrase also present in the enzyme broths, although not included in the modeling). These are mainly sucrose, raffinose and stachyose. Pectin (or pectinase-hydrolyzable carbohydrate, $\alpha_p$) and hemicellulose (or xylanase-hydrolyzable carbohydrate, $\alpha_x$) made up the major portions of the insoluble carbohydrate, 32% and 28%, respectively. They are the logical targets of enzymatic hydrolysis for separating the insoluble carbohydrate from the remaining soy protein. For maximizing production of monomeric carbohydrate, either for easy animal digestion or for use as readily fermentable substrate, the high portion (27%) of $\alpha$-galactosidase-hydrolyzable oligosaccharides is also an important hydrolysis target. Among the enzymes for these 3 targets, i.e., pectinase, xylanase and $\alpha$-galactosidase, the best-fit value of half-maximum enzyme loading constant (K) is the highest for pectinase, requiring 14.7 U/g SF to achieve 50% conversion of the pectin present, as compared to 3.15 (U/g SF) xylanase and 1.15 (U/g SF) $\alpha$-galactosidase for 50% conversion of their responsible portions of soy carbohydrate. The low value of $K_g$ may be because $\alpha$-galactosidase acts on soluble substrates, which are more accessible and do not cause enzyme denaturation by irreversible binding as the other solid substrates do. These K values are valuable to know, as they offer a guideline for the optimal enzyme mixture composition to be produced in fungal fermentation and/or used for soy flour carbohydrate hydrolysis. The model-fitted K value for cellulase ($K_c$) is 27.5 FPU/g SF, even much higher than $K_p$. This is rather surprising since the cellulase-hydrolyzable portion ($\alpha_c$) is only 4.3% and, as a rule of thumb, about 10 FPU per g substrate is typically used for lignocellulosic hydrolysis. There are several possible reasons for this high $K_c$ value: (1) pretreatment is normally required to lower the crystallinity of cellulose prior to enzymatic hydrolysis while SF was not pretreated in this study; (2) the small amount of cellulose may be surrounded by protein and other major carbohydrate, blocking its easy access by cellulase; and (3) cellulose hydrolysis contributes minimally to total conversions, rendering the model fitting inaccurate for $K_c$. Nonetheless, because of the small fraction of cellulose present, cellulase effect is the least important for the overall hydrolysis outcome.

Modeling for Kinetic Hydrolysis Performance

The best-fit parameters of the kinetic models described by Equations (3) and (4) are given in Table 3.

TABLE 3

Exemplary best-fit parameters for the kinetic hydrolysis models given in Formula 4 and Formula 5.

| Parameters in Formula 4 for total carbohydrate conversion | | | | | |
|---|---|---|---|---|---|
| r | 0.212 | | | | |
| $\alpha_0$ (%) | 35.7 | | | | |
| $k_c$ | 0.47 | $m_c$ | 0.147 | $\tau_{dc}$ (h) | 2540 |
| $k_x$ | 3.97 | $m_x$ | 0.266 | $\tau_{dx}$ (h) | 5738 |
| $k_p$ | 2.18 | $m_p$ | 0.339 | $\tau_{dp}$ (h) | 1220 |
| Parameters in Formula 5 for reducing sugar conversion | | | | | |
| r | 0.212 | | | | |
| $\alpha_{0rs}$ (%) | 7.8 | | | | |
| $k_c$ | 0.46 | $m_c$ | 0.138 | $\tau_{dc}$ (h) | 2540 |
| $k_x$ | 3.76 | $m_x$ | 0.247 | $\tau_{dx}$ (h) | 5228 |
| $k_p$ | 1.85 | $m_p$ | 0.327 | $\tau_{dp}$ (h) | 1320 |
| $k_g$ | 3.98 | $m_g$ | 0.494 | $\tau_{dg}$ (h) | 2668 |

For both models the r value is 0.212, indicating a relatively significant effect of soy flour concentration on the carbohydrate hydrolysis. The effect of soy flour loading was also tested, up to 375 g/L, as shown in Table 4.

TABLE 4

Experimental and model-predicted conversions at various soy flour concentrations.

| Soy flour concentration (g/L) | Experimental conversion (%) | | Model-predicted conversion (%) | |
|---|---|---|---|---|
| | Reducing sugar | Total soluble carbohydrate | Reducing sugar | Total soluble carbohydrate |
| 275 | 72.0 ± 1.1 | 73.4 ± 0.9 | 72.5 ± 1.6 | 73.0 ± 0.9 |
| 300 | 70.2 ± 1.9 | 73.0 ± 0.8 | 72.0 ± 1.4 | 72.0 ± 0.6 |
| 325 | 68.5 ± 0.9 | 70.6 ± 1.2 | 70.8 ± 0.7 | 71.8 ± 1.6 |
| 375 | 66.9 ± 0.7 | 69.3 ± 1.5 | 68.8 ± 1.1 | 67.3 ± 1.3 |

The model predicted the experimentally obtained conversions well even at substantially higher levels of substrate loading. As described elsewhere herein, the kinetic parameters can be different in the equations for TC and RS conversions. For each enzyme group, the TC conversion kinetics can be faster if the soluble oligomeric carbohydrate generated cannot be immediately hydrolyzed to monomers; in this case, the increase of reducing sugar conversion requires longer reaction time. This appears to be the case for xylanase- and pectinase-dependent hydrolysis in Table 3, where $k_x$, $k_p$, $m_x$, and $m_p$ values are larger for total carbohydrate conversion than for reducing sugar conversion. Among pectinase, xylanase and cellulase, xylanase have the largest k and m values followed by pectinase, indicating that xylanase and pectinase has the strongest effect on total carbohydrate conversion. This is partly because they make up the larger fractions of insoluble soy flour carbohydrate. Highest k value of xylanase also indicates that hemicellulose degradation is relatively faster than other group of carbohydrates. Larger k value pectinase also suggest that it is important for the overall carbohydrate conversion. Based on other studies of the fractionated extraction of soybean carbohydrate, it is believed that protein and other carbohydrate are trapped by the pectic structural polysaccharides. Breaking down pectin is important to the accessibility of enzymes to more carbohydrate. The m value for cellulase is particularly low, implying that cellulase is not very effective in hydrolyzing the cellulose in soy flour carbohydrate. This can be partly because the soy flour was not subjected to any pretreatment prior to the hydrolysis in this study, while pretreatment is generally required for enzymatic hydrolysis of cellulose (at least for lowering the crystallinity). This is also consistent with other reports that cellulose is the least accessible to enzyme hydrolysis; cellulose becomes accessible only after other carbohydrates are largely hydrolyzed. For the reducing sugar conversion model, α-galactosidase has highest k value: 3.98. High α-galactosidase activity is critical to monomerization of the relatively large fractions of stachyose and raffinose (and possibly other similar oligosaccharides released by other enzymes).

Characteristic time parameter $\tau_d$ for each enzyme could give valuable insight on the enzyme stability or the substrate accessibility based on the structural changes or availability over time. $\tau_d$ values for xylanase are the largest, >5000 h. The values for α-galactosidase and cellulase (>2000 h) are also very large. The issues of enzyme stability and substrate change are therefore insignificant for the hydrolysis by these 3 enzymes, within the timeframe of interest to this study (no more than 48 h). The $\tau_d$ values for pectinase are however smaller than others: 1220 h for total carbohydrate conversion and 1320 h for reducing sugar conversion. This suggests that pectinase is less stable under the reaction condition (particularly the relatively high temperature, 50° C.) and/or the accessibility/hydrolyzability of pectin decreases more significantly with time. Pectinase has indeed been reported to be much less stable at higher temperatures (50° C.) than cellulase and xylanase.

The model predicted conversions, with the best-fit parameters given in Table 3, were determined. The correlations were reasonably good, with $R^2$ values of 0.93 and 0.96 for total carbohydrate and reducing sugar conversions, respectively. The Fisher's F-test gave very low p values (<<0.00001) for both total carbohydrate and reducing sugar conversion models, also confirming the high significance of the models.

Effect of Enzymes from Different Fungal Species

The kinetic models with best-fit parameters described the experimental results reasonably well for many systems. The experimentally measured and model predicted hydrolysis conversion profiles were compared for enzyme broths produced by different fungal species: *A. niger*, *T. reesei*, and *A. aculeatus*, and a mixture of *A. niger* and *T. reesei* broths. The models were shown to describe the experimental results for enzymes from all three species with reasonable accuracy. However, the models under-predicted the hydrolysis outcomes of the mixed enzymes of *A. niger* and *T. reesei*. This underestimation, caused by the synergy between the two enzyme mixtures, occurred consistently for the mixed systems with 30%-80% *A. niger* enzyme broth and 20%-70% *T. reesei* enzyme broth.

The *T. reesei* enzymes gave much lower total carbohydrate and reducing sugar conversions than the *A. niger* enzymes, i.e., 58% and 37%, respectively, versus 81% and 76%. The *T. reesei* enzymes contained higher cellulase and xylanase activities but lower pectinase and α-galactosidase activities. For Formulas (1) and (2), the half maximum enzyme loading constant for xylanase $K_x$ was only 3.15 U/(g SF) while the xylanase activity used from either *T. reesei* or *A. niger* enzymes was excessively higher: 191 U/(g SF) for the former and 171 U/(g SF) for the latter. Complete xylan hydrolysis was expected from certain of the systems. The low maximum hydrolysis fraction contributed by cellulase, i.e., 4.3% (Table 2), further dictated that the higher cellulase activity in *T. reesei* enzymes (2.4 FPU/ml) than in *A. niger* enzymes (0.69 FPU/ml) would not influence the overall hydrolysis extent significantly. Accordingly, the two enzymes gave different conversions only because of their different pectinase and α-galactosidase activities. The half maximum enzyme loading constant for α-galactosidase $K_g$ was 1.15 U/(g SF). The low α-galactosidase (0.33 U/ml) in *T. reesei* enzymes resulted in only 37% conversion to reducing sugars, insufficient to hydrolyze the 58% soluble carbohydrate found in the hydrolysate; on the other hand, the significantly higher α-galactosidase activity (8.1 U/ml) in *A. niger* enzymes monomerized almost all soluble carbohydrate, giving similar reducing sugar conversion (76±2%) and total carbohydrate conversion (81±2%). The half maximum enzyme loading constant for pectinase $K_p$ was 14.7 U/(g SF). The pectinase activities used in FIG. 5 were insufficient from both enzymes: 7.2 U/(g SF) for *A. niger* and 2.4 U/(g SF) for *T. reesei*, but the different activities made a significant difference in the total carbohydrate conversion, i.e., 81% for *A. niger* and 58% for *T. reesei*. Nevertheless, the maximum conversion of 81% achieved by the *A. niger* enzymes, in spite of having satisfactory xylanase and α-galactosidase activities, was limited by the pectinase activity. Producing carbohydrate mixtures with higher pectinase activities is an effective path in improving the process of enzyme hydrolysis of soy carbohydrate for preparing soybean meal as a high-quality protein source for animal feed. Being largely monomerized, the carbohydrate in the hydrolysate makes a good energy source for animal feed without indigestibility concern. However, if no carbohydrate-rich hydrolysate is separated from the protein-rich solids, the protein content of final dry product would be essentially the same as the starting meal/flour (about 50%). Certain portion of the hydrolysate has to be removed to achieve the desired protein enrichment of soy protein product for a specific application. Centrifugation can separate the hydrolysate from the wet protein-rich solids. The hydrolysate collected can be used as fermentation substrate for producing bioethanol and specialty chemicals such as succinic acid and fatty acids. The hydrolysate has also been shown to support good production of arabitol, a five-carbon low-calorie sugar alcohol, by fermentation using *Debaryomyces hansenii*.

Example 11

Materials and Equipment

Defatted soy flour (7B soy flour) and soy hulls were provided by Archer Daniel Midland (Decatur, Ill.). HCl (concentrated acid, 37.4%) and NaOH (98.8%) were purchased from Fisher Scientific (Waltham, Mass.). NaN3 (>99%) and dinitrosalicylic acid (DNS, 98%) were purchased from Sigma-Aldrich (St. Louis, Mo.). *A. niger* (NRRL 341) and *T. reesei* Rut-C30 (NRRL 3469) seed cultures were obtained from the United States Department of Agriculture (USDA) Agricultural Research Service (ARS) Culture Collection. Two 3 L Bioflo 110 fermentors (New Brunswick Scientific Co., Edison, N.J.) were used for enzyme production by fermentation. Absorbance was measured using a UV/Vis spectrophotometer (UV-1601, Shimadzu Corporation, Columbia, Md.). The hydrolysis experiments were conducted in a shaker (Thermo Scientific MaxQ 5000 Incubating/Refrigerating floor shaker, Ashville, N.C.). The centrifuge used was Sorvall Legend X1R from Thermo Scientific (Waltham, Mass.)

Enzyme Solutions

Fungal fermentation to produce enzyme broth was conducted. Enzyme solutions used in this study were prepared from the cell-free supernatants collected by centrifugation of the fermentation broths at 8000 rpm (7440×g) for 10 min. Cellulase, xylanase, pectinase and α-galactosidase activities of the cell free broths were measured. Known methods were used for cellulase, xylanase, pectinase, and α-galactosidase activity measurements.

Enzymatic Hydrolysis

Hydrolysis experiments were made in 250 ml Erlenmeyer flasks; each flask contained a suspension of soy flour in 40 ml enzyme solution (not 40 ml in total volume). 0.5 g/L NaN3 was added to prevent microbial contamination. The enzyme solution was prepared by diluting the supernatant of fermentation broth to achieve the particular enzyme/soy flour ratio studied. The soy flour amount was also added according to the specific loading studied. Mixture pH was adjusted with 5M HCl to the studied pH. Hydrolysis was allowed to take place for 48 h in a shaker operating at 250 rpm. Different shaker chamber temperatures were set in different hydrolysis batches to study the temperature effect. Periodical samples were taken and centrifuged to separate the solids and the liquid supernatant; both fractions were frozen for later analyses. The factors investigated were in the following ranges: soy flour concentration, 150-350 g/L; enzyme/soy flour ratio, 0-2 ml solution/g; temperature, 40-60° C.; and pH, 3.2-6.4.

Analytical Methods

The supernatants collected were analyzed for concentrations of reducing sugar and total carbohydrate. Reducing sugar concentration was measured with the dinitrosalicylic (DNS) acid method. Total carbohydrate concentrations were measured using the phenol sulfuric acid colorimetric method. This method is based on the principle that carbohydrate reacts with sulfuric acid to produce furfural derivatives, which then react with phenol to develop a characteristic color. Total carbohydrate concentration was determined from the absorbance reading according to a calibration curve obtained with standard glucose solutions, following the same procedure as described above. Protein contents in the defatted soy flour and enriched protein products were measured by the Kjeldahl method. Ash and fatty acid content measurements were done by the University of Missouri Agricultural Experimental Station, using the standard NREL method (23) for ash content analysis in biomass and the Soxhlet hexane extraction method for the crude fat content.

Experimental Design

Response surface methodology (RSM) was used for modeling and analyzing the enzymatic hydrolysis outcomes by the two enzyme broths (*A. niger* and *T. reesei*) used. Reducing sugar and total carbohydrate conversions (%) were the two responses. pH, temperature, enzyme/soy flour ratio, and soy flour loading were the independent variables. Each variable was studied at five levels (−α, −1, 0, 1, +α) as listed in Table 5.

TABLE 5

Code levels and actual values used for each variable in the central composite experimental design.

| Independent Variable | Unit | Symbol | Code level and actual value | | | | |
|---|---|---|---|---|---|---|---|
| | | | −α | −1 | 0 | +1 | +α |
| pH | pH | | 3.2 | 4.0 | 4.8 | 5.6 | 6.4 |
| Temperature | ° C. | T | 40 | 45 | 50 | 55 | 60 |
| Enzyme/Soy flour | ml/g | E | 0 | 0.5 | 1.0 | 1.5 | 2.0 |
| Soy flour loading | g/L | S | 150 | 200 | 250 | 300 | 350 |

Central composite design (CCD) of four independent factors was used as the experimental design approach, summarized in Table 6.

TABLE 6

Experimental design matrix for the four independent variables.

| Run | pH | T (° C.) | E (ml/g) | S (g/L) |
|---|---|---|---|---|
| 1 | 4 | 45 | 1.5 | 250 |
| 2 | 4 | 55 | 1.5 | 200 |
| 3 | 4.8 | 50 | 1 | 250 |
| 4 | 4 | 45 | 0.5 | 200 |
| 5 | 3.2 | 50 | 1 | 250 |
| 6 | 5.6 | 45 | 1.5 | 300 |
| 7 | 4.8 | 50 | 1 | 250 |
| 8 | 4.8 | 50 | 1 | 150 |
| 9 | 4.8 | 50 | 1 | 250 |
| 10 | 4.8 | 50 | 0 | 250 |
| 11 | 6.4 | 50 | 1 | 250 |
| 12 | 4.8 | 60 | 1 | 250 |
| 13 | 4 | 45 | 0.5 | 300 |
| 14 | 4.8 | 50 | 1 | 250 |
| 15 | 4 | 55 | 0.5 | 200 |
| 16 | 4.8 | 50 | 2 | 250 |
| 17 | 4.8 | 50 | 1 | 300 |
| 18 | 5.6 | 55 | 1.5 | 300 |
| 19 | 4.8 | 50 | 1 | 250 |
| 20 | 4 | 55 | 1.5 | 300 |
| 21 | 4.8 | 40 | 1 | 250 |
| 22 | 4.8 | 50 | 1 | 350 |
| 23 | 4 | 45 | 1.5 | 200 |
| 24 | 5.6 | 55 | 1.5 | 200 |
| 25 | 4 | 55 | 0.5 | 300 |
| 26 | 5.6 | 45 | 0.5 | 300 |
| 27 | 5.6 | 55 | 0.5 | 250 |
| 28 | 5.6 | 55 | 0.5 | 200 |
| 29 | 5.6 | 45 | 0.5 | 250 |
| 30 | 5.6 | 45 | 1.5 | 200 |

All experiments were done in triplicate and the average values of reducing sugar and total carbohydrate conversions were taken as the responses. Soluble carbohydrate conversion (YTC,%) and reducing sugar conversion (YRS,%) were calculated as: YRS=Rs/Tc×100 and YTC=Ts/Tc×100. RS and TS are concentrations of the soluble reducing sugar and total soluble carbohydrate, respectively, in the hydrolysate supernatant, and TC is the initial (soluble and insoluble) total carbohydrate concentration introduced with the soy flour. The influence of variables on response was analyzed using the multiple regression method with two quadratic polynomial equations. Analysis of variance was conducted to evaluate the effects of variables and their interactions. Model coefficients were analyzed for significance. Insignificant terms were eliminated and the reduced model was adjusted. Response surface plots and the corresponding contour plots were then constructed according to the developed models to visualize the variable-response relationship.

Design-Expert 9 (Stat-Ease, Inc., Minneapolis, Minn.) was used for the aforementioned regression analysis and for generating response surface plots.

Enzyme Hydrolysis

Carbohydrate conversions over time by *A. niger* and *T. reesei* enzymes to soluble reducing sugars and total soluble carbohydrates, i.e., YRS and YTC, were found for the following hydrolysis condition: enzyme-to-soy flour ratio, 1 ml/g; soy flour loading, 250 g/l; pH, 4.8; and temperature, 50° C. The *A. niger* broth used in this study contained 0.49 U/ml cellulase, 143.27 U/ml xylanase, 3.8 U/ml pectinase and 3.1 U/ml α-galactosidase. Corresponding activities for the *T. reesei* broth were 1.38 U/ml, 109.45 U/ml, 1.9 U/ml and 0.4 U/ml, respectively. The *A. niger* enzyme broth gave higher conversions than the *T. reesei* broth, apparently because of the higher enzyme activities (except for the cellulase) in the *A. niger* broth. For both broths YTC values were larger than YRS but the differences were clearly larger with the *T. reesei* enzymes. The larger differences indicated higher amounts of soluble oligomeric carbohydrates in the hydrolysate, i.e., less complete monomerization. Accordingly, the *A. niger* enzyme broth was more effective than the *T. reesei* broth (on per unit volume basis), and the *T. reesei* broth was particularly deficient in the enzymes (e.g., α-galactosidase) for hydrolyzing the oligomeric carbohydrates to monomers.

For both enzyme preparations, YTC reached the maximal levels by about 24 h while YRS needed about 48 h to approach the plateaus. 48 h was chosen for all the subsequent data analysis. Then, further work was done for optimizing reaction temperature (T), pH, enzyme-to-soy flour ratio (E), and soy flour loading (S). The choice of the relatively long time, 48 h, for comparison allowed the optimization to be done with the maximal conversions (at least nearly so for YRS) obtainable.

Best-Fit Models for Hydrolysis Conversions

ANOVA analysis was done for the best-fit quadratic models for the YRS and YTC obtained with *A. niger* and *T. reesei* enzymes. Results showed large F values from the Fisher F-test (>30 for all cases), very low p values, <0.0001, and close-to-1 $R^2$ values (>0.96). The analysis demonstrated high significance of the models developed. The models are given in Formulas (9)-(12), with coded variables: $pH_c=(pH-4.8)/0.8$, $T_c=(T-50)/5$, $E_c=(E-1)/0.5$, and $S_c=(S-250)/50$.

For *A. niger*, $$Y_{RS}=66.02+1.99\ pH_c-2.36T_c+10.07E_c-2.08S_c-7.63(pH_c \times T_c)+4.43(pH_c \times E_c)-10.98\ pH_c^2-7.84T_c^2-3.35E_c^2 \quad (9)$$

$$Y_{TC}=70.79+0.93\ pH_c-0.47T_c+7.93E_c-1.45S_c-4.45(pH_c \times T_c)-0.64(pH_c \times E_c)+0.03(pH_c \times S_c)-5.11\ pH_c^2-4.34T_c^2-2.04E_c^2 \quad (10)$$

were the developed models, and for *T. reesei*, $$Y_{RS}=27.1+1.28\ pH_c+0.73T_c+6.29E_c-0.32S_c-1.85(pH_c \times T_c)+2.68(pH_c \times E_c)+1.55(T_c \times E_c)-4.11\ pH_c^2-3.09T_c^2-4.66E_c^2 \quad (11)$$

$$Y_{TC}=58.81+0.92\ pH_c-0.95T_c+7.83E_c-2.78S_c+1.1(pH_c \times E_c)-3.41\ pH_c^2-1.96T_c^2-2.96E_c^2 \quad (12)$$

were the developed models.

Model Predicted Maximum Conversions and Optimal Operating Conditions

These model equations were used to determine the operating conditions, within the tested ranges of factor values, for achieving the maximum total soluble carbohydrate and reducing sugar conversions. A numerical optimization method available with the software package Design-Expert 9 (Stat-Ease, Inc., Minneapolis, Minn.) was used. The optimal conditions and the maximum conversions achieved are summarized in Table 7. All maximum conversions were achieved at the highest enzyme/soy flour ratio (2 ml/g) and the lowest soy flour loading (150 g/L) tested. The use of more enzyme is expected to enhance the reaction rate and completeness while a lower soy flour loading gives lower system viscosity and better mixing. The optimal pH and temperatures for maximum $Y_{RS}$ were only slightly different from those for maximum $Y_{TC}$; and the optimal conditions did not vary much for the two enzyme broths used. Within the tested variable ranges, with *A. niger* enzymes the maximum $Y_{TC}$ would reach 79.2% at pH 4.79 and 51.5° C., while the maximum $Y_{RS}$ predicted was 74.5% at pH 5.17 and 48.3° C. With the *T. reesei* enzymes, the maximum $Y_{TC}$ achievable was 68.9% at pH 4.77 and 50.1° C. while the maximum $Y_{RS}$ was only 33.7% at pH 5.12 and 50.9° C. These values confirmed that the *A. niger* enzyme broth was more effective than the *T. reesei* enzyme broth for hydrolysis of soy flour carbohydrate.

TABLE 7

Optimal conditions for maximizing reducing sugar (RS) and total soluble carbohydrate (TC) conversions.

| | | Optimum Conditions | | | |
| --- | --- | --- | --- | --- | --- |
| | | *A. niger* | | *T. reesei* | |
| Variable | Range | RS | TC | RS | TC |
| pH | 3.2-6.4 | 5.17 | 4.79 | 5.12 | 4.77 |
| Temperature (T, ° C.) | 40-60 | 48.3 | 51.5 | 50.9 | 50.1 |
| Enzyme/SF (E, ml/g) | 0-2 | 2.0 | 2.0 | 2.0 | 2.0 |
| SF loading (S, g/L) | 150-350 | 150 | 150 | 150 | 150 |
| Maximum conversion (%) | | 74.5 | 79.2 | 33.7 | 68.9 |

Single-Factor Effects

How sensitively different variables affected these conversions away from the optimal conditions was also studied. Effects of individual factors on YRS and YTC obtained with *A. niger* and *T. reesei* enzyme broths, respectively were determined with the following reference conditions (for the non-varying factors): pH 4.8, 50° C., 1.5 ml/g enzyme-to-soy flour ratio, and 200 g/L soy flour loading. For all 4 single-factor effects, the conversions by the *A. niger* broth were consistently more responsive to the operating condition changes, as compared to the conversions by the *T. reesei* broth.

pH was found to have quadratic effects on the conversions. The fungal enzyme broths contain mixtures of pectic polysaccharide degrading enzymes, cellulolytic enzymes and oligosaccharide degrading enzymes. With these enzyme mixtures, the hydrolysis outcome depends on the effectiveness of all the enzyme groups involved at the specific condition. The optimum pH values were in the range of 4.8 to 5.2 (Table 7). The reducing sugar conversion by the *A. niger* broth was shown to be much more sensitive to the pH change than the other three conversions. This suggests that the enzymes, such as α-galactosidase, responsible for degrading soluble oligosaccharides to smaller sugars are more pH sensitive near its optimum value.

Temperature also had quadratic effects on the conversions. The optimum temperatures for both *A. niger* and *T. reesei* broths were in the similar range of 48 to 52° C. For both broths, $Y_{RS}$ was slightly more temperature sensitive than the corresponding $Y_{TC}$. The conversions all increased with increasing enzyme-to-soy flour ratio (E) in the range evaluated. The increasing trends were higher with the *A. niger* broth than with the *T. reesei* broth. The trends also indicated that the conversions would still increase at enzyme-to-soy flour ratios higher than the maximum of 2 ml/g tested here, particularly for the *A. niger* broth. To confirm this, additional experiments were made at 3 ml/g and 4 ml/g ratios with the *A. niger* broth while keeping other factors at the same reference conditions. $Y_{TC}$ increased to 86% and $Y_{RS}$ increased to 83%; the increases were increasingly less linear at higher conversions.

The model-predicted effects of soy flour loading on the conversions were determined. With the *A. niger* enzyme broth, both $Y_{TC}$ and $Y_{RS}$ decreased linearly with increasing soy flour loading. At 350 g/L soy flour loading $Y_{TC}$ and $Y_{RS}$ were about 14% and 9% lower, respectively, than the corresponding conversions obtained at 150 g/L soy flour loading. The finding of parallel decreases of $Y_{TC}$ and $Y_{RS}$ suggested that the negative effect of increasing loading was mostly on the release of total soluble carbohydrate; otherwise, $Y_{RS}$ would have decreased more than $Y_{TC}$. Conceptually, the negative effect of increasing soy flour loading is probably caused by the inhibited interactions between the solid substrate and the corresponding enzyme components. One of these inhibited interactions may be the reduced accessibility of enzyme to the solid substrate reactive sites, which are increasingly blocked by the surrounding solids as the loading increases. With the *T. reesei* enzyme broth, $Y_{TC}$ also decreased linearly with increasing soy flour loading but $Y_{RS}$ was insignificantly affected. This reflected again that the *T. reesei* broth was highly deficient in the enzyme components for hydrolyzing soluble oligosaccharides.

Even though high substrate loading negatively impacted the hydrolysis yield, it can be beneficial for the process economics because of two reasons. First, high substrate loading reduces the working volume and potentially the operation cost. Second, the hydrolysate produced with a high substrate loading can have a higher carbohydrate concentration. This hydrolysate requires less or no subsequent costly concentrating, prior to use as fermentation substrate. Future analysis on overall process economics is necessary to address these compromising effects of the soy flour loading level.

Interaction Effects

Two dimensional contour plots were determined for the total soluble carbohydrate and reducing sugar conversions. Certain pairs of factors were identified to have significant cross interactions. Single-factor effects have already been described; the main purpose here is to show how the changes of one factor would affect the effect of the other factor on the response.

For the determined contour plots, while the two factors of interest were varied in a plot, the other two factors were kept constant at the reference conditions, i.e., pH=4.8, T=50° C., E=1.5 ml/g, and S=200 g/L. For both enzyme broths, the pH×T effects on conversion to reducing sugar are the clearest to see. $Y_{RS}$ clearly favors lower pH values if higher reaction temperatures are used. A same trend, but to a much lower extent, was seen for the pH×T effect on the conversion to total soluble carbohydrate by the *A. niger* broth. For the pH×S effect on $Y_{TC}$ by the *A. niger* broth, the favorable pH is shown to shift slightly to higher values for systems with lower soy flour loadings while pH at higher than 4.8 has clearer negative effects for systems with high soy flour loadings. The interaction effects are not clear for the other plots, which all included the enzyme-to-SF ratio (E) as one of the factors. The strong single-factor effects of E seem to mask its weaker interaction effects with the other factors, in the ranges evaluated.

In summary, a higher enzyme-to-SF ratio results in better hydrolysis conversions as expected. However, an overly increase of enzyme loading does not linearly increase the hydrolysis. This phenomenon may be attributed to several factors. One is the decrease in readily accessible reactive sites of soy flour to all the enzyme molecules at high enzyme-to-SF ratios. Another factor is related to the non-homogeneous reactive sites of SF: to increase the conversion requires the enzyme to act on less reactive sites of the solid substrate. Enzyme deactivation over time due to adsorption on nonreactive sites may also occur to larger extents at higher enzyme-to-SF ratios. Use of higher substrate concentrations has some negative effects on conversions. But the hydrolysates from these systems have higher soluble carbohydrate concentrations and, therefore, require less or no further concentrating for subsequent use, e.g., as fermentation feedstock.

Protein Enrichment

Soy flour protein content was enriched by the enzymatic carbohydrate conversion. The compositions of the original defatted soy flour and the solid product collected after 48 h enzymatic conversion are given in Table 8, for two reaction conditions: one at the optimal condition, i.e., pH=4.8, T=50° C., E=2 ml/g (enzyme-to-SF ratio) and S=150 g/l (SF loading), the other at E=1 ml/g and S=250 g/l (lower E, higher S).

TABLE 8

Compositions of defatted soy flour and enriched protein products by *A. niger* and *T. reesei* enzyme broths.

| Component | Defatted soy flour | Protein concentrate[2] E = 2 ml/g, S = 150 g/l | | Protein concentrate[2] E = 2 ml/g, S = 150 g/l | |
|---|---|---|---|---|---|
| | | *A. niger* | *T. reesei* | *A. niger* | *T. reesei* |
| Protein | 53.9 ± 0.9 | 74.6 ± 0.6 | 74.1 ± 0.7 | 68.7 ± 0.6 | 68.1 ± 0.5 |
| Carbohydrate | 34.9 ± 1.1 | 17.2 ± 0.9 | 17.7 ± 0.5 | 23.1 ± 0.9 | 23.7 ± 1.1 |
| Insoluble | 20.7 ± 0.7 | 11.3 ± 0.8 | 12.2 ± 0.4 | 14.0 ± 0.7 | 15.1 ± 0.8 |
| Soluble RS[3] | 11.6 ± 0.5 | 5.9 ± 0.4 | 3.0 ± 0.4 | 9.1 ± 0.6 | 4.7 ± 0.6 |
| Other solubles[4] | 2.8 ± 0.2 | 0.0 | 2.5 ± 0.3 | 0.0 | 3.9 ± 0.4 |
| Ash | 7.5 ± 0.4 | 5.5 ± 0.4 | 5.6 ± 0.3 | 5.6 ± 0.5 | 5.7 ± 0.4 |
| Crude fat | 3.5 ± 0.2 | 2.7 ± 0.2 | 2.6 ± 0.3 | 2.6 ± 0.4 | 2.5 ± 0.3 |

With the optimal reaction condition, the protein content was increased from 54% to 74-75% and the carbohydrate content was decreased from 35% to 17-18%, where the slightly higher protein content and lower carbohydrate content were achieved by the *A. niger* enzyme broth. The ash and fat contents were also lowered rather similarly by the two fungal enzyme broths. With the lower E, higher S condition, the protein content was increased to 68-69% and the carbohydrate content was decreased to 23-24%. The purpose of protein enrichment was clearly achieved by the enzymatic process, without very significant differences by the two fungal enzyme broths.

The enriched protein products reported in Table 8 were collected by centrifugation without washing. They had about 28±2% liquid, which contained the same soluble carbohydrates as in the hydrolysate. Therefore, the carbohydrate contents given include both insoluble and soluble carbohydrates, and the latter include monomers and oligomers. The values of "other solubles" given in Table 8 represent the minimal contents of soluble oligomeric carbohydrates (since oligosaccharides can also have reducing ends). With both reaction conditions, the *A. niger* broth completely monomerized the soluble carbohydrates while the *T. reesei* broth left approximately half of the soluble carbohydrates as oligomers (2.5% and 3.9% "other solubles", respectively, with the different reaction conditions). While the insoluble carbohydrates are mostly dietary fibers, the soluble oligosaccharides tend to cause the indigestibility problem. The "other solubles" content in the *T. reesei* broth-treated product at the lower E, higher S condition was even much (~40%) higher than that in the original soy flour. Therefore, while the two enzyme broths would give similar protein enrichment effects, the *A. niger* broth essentially eliminated the indigestibility concern while the *T. reesei* broth could worsen it.

Example 11

Soy meal concentration in the enzymatic processing is the amount of soy meal processed in a unit volume of the enzyme-containing liquid, often given in the unit of g/L. This solid substrate concentration is sometimes termed as the solid loading. Use of a higher soy meal concentration offers the potential of getting a higher concentration of hydrolyzed, soluble carbohydrate in the hydrolysate. Hydrolysate with a higher carbohydrate concentration requires less or no further processing to concentrate for its subsequent use, for example, as fermentation substrate or chemical reactant for production of value-added products. Use of a higher soy meal concentration also means a smaller reactor volume and a lower liquid amount are required for processing the same total amount of soy meal. A smaller reactor volume translates to a lower capital cost and, potentially, a lower operating cost. The lower liquid amount used translates to less wastewater to handle.

Figure 9:
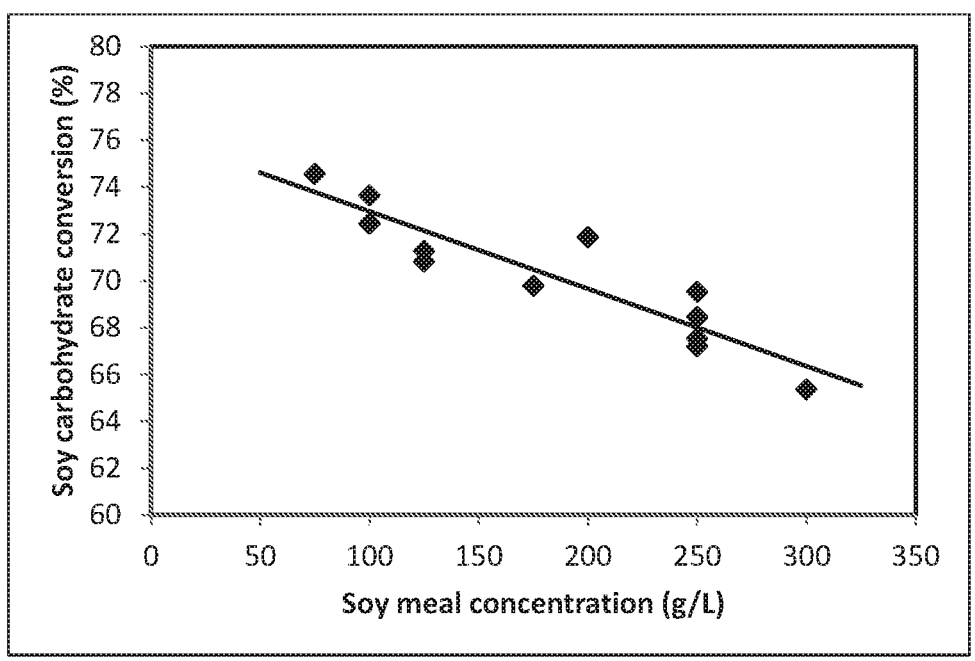
FIG. 9 is a graph showing an example of the effect of soy meal concentration on the conversion of carbohydrate in soy meal to soluble carbohydrate in the hydrolysate.

A series of experiments was made to determine the effect of different soy meal concentrations on the outcome of enzymatic processing, evaluated in terms of the conversion percentage of soy carbohydrate to the total soluble carbohydrate in the resultant hydrolysate. The enzymatic processing experiments were done with different soy meal concentrations while keeping a constant "ratio" of added enzyme concentration to the soy meal concentration used. Experiments were done at 50° C. temperature, pH 4.8, and the fixed enzyme-to-soy ratio of 1 ml enzyme mixture per g of soy meal. The soy carbohydrate conversions obtained after 48 hours of enzymatic processing are shown in FIG. 9 for the different soy meal concentrations tested. The conversion decreased from 74% to 65% almost linearly with the increase of soy meal concentration from 75 g/L to 300 g/L.

Example 12

Figure 10:
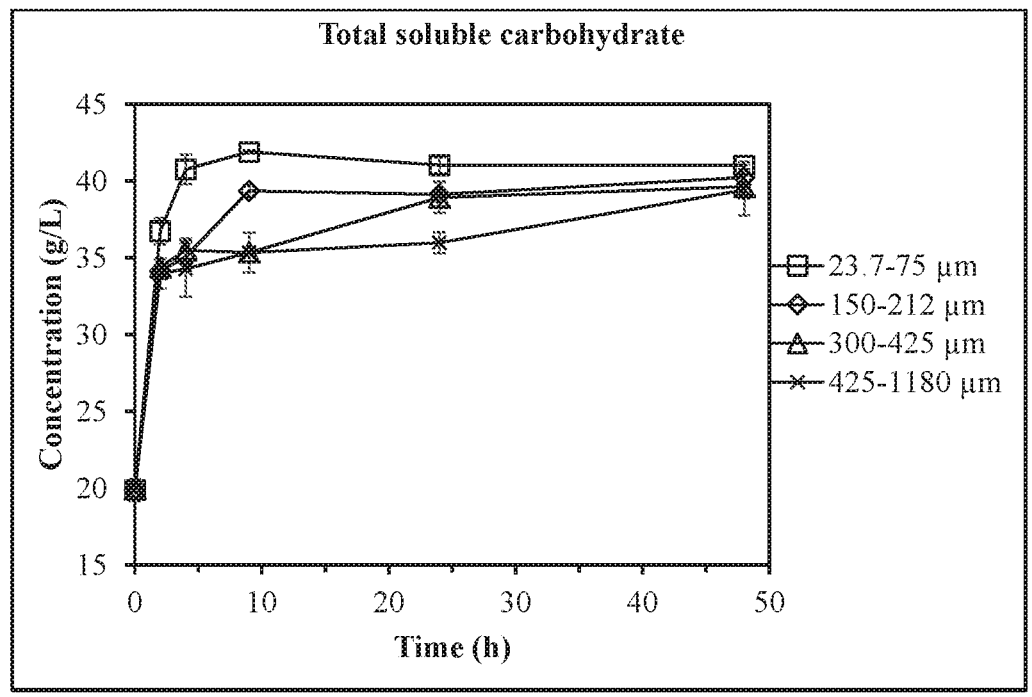
FIG. 10 is a graph showing an example of profiles of total soluble carbohydrate concentration in hydrolysate for soy meal of different particle size ranges.
Figure 11:
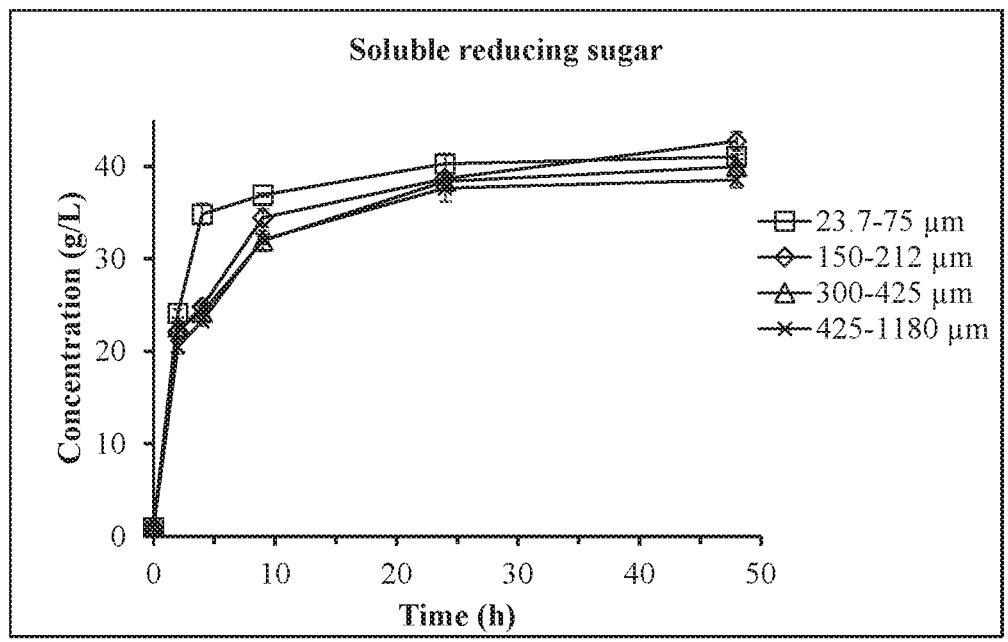
FIG. 11 is a graph showing an example of profiles of reducing sugar concentration in hydrolysate for soy meal of different particle size ranges.

The enzymatic soy meal processing can be further improved by adjusting the size of the solid particles. For each particle size range listed in FIGS. 10 and 11, duplicate systems were evaluated. Temperature and pH were maintained at 50° C. and 4.8, respectively, which were the optimum conditions. 250 g/L soy meal was processed in a 250 ml Erlenmeyer flask containing 40 ml liquid, which included 1 ml enzyme per g soy meal. The enzyme broth used contained α-galactosidase activity 11.5±0.49 U/ml and pectinase activity 10.05±0.4 U/ml, and other enzyme components with undetermined activities. For all the systems, the processing time was up to 48 h. Periodical samples were taken from all systems at 0, 2, 4, 9, 24 and 48 h, and the soluble carbohydrate concentrations in the collected hydrolysates were measured by the phenol-sulfuric acid assay for total carbohydrate and by the standard DNS assay for reducing sugar. The results are shown in FIGS. 10 and 11.

Results clearly showed the benefits of using the particle size in the range of 23.7-75 μm, where much faster enzymatic processing rates were achieved. In about 4 h, the total soluble carbohydrate already reached approximately the highest achievable concentration. It would take longer, about 10-20 h, to achieve the same for soluble reducing sugar but this situation could be improved by the use of hydrolysate recycle, as described in the previous section, to accumulate higher α-galactosidase activities. Shortening the processing time to 4 h (from the previous 48 h period) would have tremendous benefits in reducing the processing costs.

Example 13

The enzymatic processing outcomes can be further improved by toasting or heating the soy meal prior to the enzymatic processing.

The following soy flour samples were evaluated, all from ADM (Archer-Daniels-Midland Company): Toasted Nutri soy, Bakers soy, and 7B grade soy. Protein, fat, total dietary fiber and carbohydrate contents were practically same for these grades. They differed mainly in prior heat treatment: Toasted Nutri soy was more heat treated, Bakers soy was lightly heat treated, and 7B grade was minimally heat processed. Enzymatic processing was compared at 50° C. and pH 4.8 for 48 h. Measured activities of the enzyme broth used were given in Table 9. Soy meal concentration was 250 g/L, in 250 ml Erlenmeyer flasks with 40 ml liquid volume.

TABLE 9

Enzyme activities of the broth used for evaluation of soy flour with different prior heat treatment extents.

| Enzyme | Activity |
|---|---|
| Cellulase (FPU/mL) | 0.50 ± 0.01 |
| Xylanase (U/mL) | 171.7 ± 14.5 |
| Pectinase (U/mL) | 5.50 ± 0.11 |
| α-galactosidase (U/mL) | 8.02 ± 0.31 |
| Protease (U/ml) | 122.6 ± 6.2 |
| Sucrase (U/mL) | 5.48 ± 0.01 |

After the hydrolysis, solid and liquid fractions were separated by centrifugation and then soy protein isolate (SPI) was precipitated from the liquid fraction by heating the liquid fraction in boiling water for 30 minutes. After collecting the SPI by centrifugation, remaining concentration of protein (including peptides and amino acids) in the hydrolysate was measured by the total nitrogen assay. This remaining soluble protein constitutes the protein "loss" (unrecovered in soy protein concentrate or soy protein isolate) of the processing. The same procedure was followed for each of the soy meal products but no enzyme was added to the liquid in this systems. These "control" systems were subjected to enzyme-free processing.

The protein "loss" concentrations remaining unrecovered in the hydrolysate after SPC and SPI separation are shown in Table 10.

TABLE 10

Unrecovered protein concentrations in hydrolysate for soy flour with different extents of prior heat treatment (250 g/L soy flour loading).

| Soy Product | Protein "loss" concentration in hydrolysate (g/L) | |
|---|---|---|
| | Control (Enzyme-free) | Enzymatic processing |
| Toasted Nutri Soy | 9.5 | 15.8 |
| Bakers Soy | 16.5 | 20.8 |
| 7B grade Soy | 25.1 | 29.7 |

Results showed that the predominant portion of the protein "loss" occurred in the enzyme-free controls also. The additional protein loss due to enzymatic processing was rather small. Results further showed that less protein loss occurred with higher extent of heat treatment.

From the results described above, heat treatment can significantly reduce the protein loss. The 7B grade soy flour from ADM was minimally heat processed. So this soy flour was used as the base material and subjected to additional heat treatment to directly demonstrate the beneficial effects of heat treatment on not only protein loss but also other enzymatic processing outcome such as soluble carbohydrate production during the processing. As an example, the additional heat treatment of 7B grade soy flour was done by dry heating in an oven at 160° C. for 2 h. Enzymatic processing was done at the same conditions as before but with the enzyme broth of the measured activities shown in Table 11. Control systems subjected to enzyme-free processing were again included for clear demonstration. In addition to the total soluble carbohydrate measurement by the phenol-sulfuric acid assay and the reducing sugar measurement by the DNS assay (both assays use glucose as a standard), concentrations of some major sugars were determined by using HPLC with a SUPELCOGEL Pb column (Column operating condition: 80° C., mobile phase flow rate 0.5 ml/min).

TABLE 11

Enzyme activity of the broth used for demonstration of heat treatment effect on the 7B grade soy flour.

| Enzyme | Activity |
|---|---|
| Cellulase (FPU/mL) | 0.65 |
| Xylanase (U/mL) | 302 |
| Pectinase (U/mL) | 6.06 |
| α-galactosidase (U/mL) | 7.80 |
| Sucrase (U/mL) | 4.91 |

The protein loss concentrations in hydrolysate are shown in Table 12.

TABLE 12

Unrecovered protein concentrations in hydrolysate for 7B grade soy flour without and with additional (2 h) heat treatment and their corresponding enzyme-free processing controls.

| Sample | | Protein concentration in hydrolysate (g/L) |
|---|---|---|
| Additional heat treatment | Enzymatic processing | |
| + | − (Control) | 10.0 |
| + | + | 12.1 |

TABLE 12-continued

Unrecovered protein concentrations in hydrolysate for 7B grade soy flour without and with additional (2 h) heat treatment and their corresponding enzyme-free processing controls.

| Sample | | Protein concentration in hydrolysate (g/L) |
|---|---|---|
| Additional heat treatment | Enzymatic processing | |
| − | − (Control) | 25.6 |
| − | + | 29.3 |

In Table 12 the systems are arranged in the order of increasing protein loss. It is clear that, with or without enzyme present in the processing, the systems subjected to the additional 2 h heat treatment had far lower (⅓ to ½) protein concentrations unrecovered in the remaining hydrolysate, as compared to the systems without the additional heat treatment. Again, the enzyme-related increase in protein loss was comparatively low.

The more detailed comparison to demonstrate the benefits of the heat treatment effect is made in Table 13 for the protein loss in hydrolysate. The protein contents given here were the value in the soy product obtained by simply drying the wet mass collected. The predominant non-protein component in the dry soy product is the hydrolyzed monosaccharides present in the trapped liquid. If desirable, the liquid can be squeezed (or washed) out to have products of much higher protein contents. With much less protein loss, protein contents in the SPC obtained from the soy flour with additional 2 h heat treatment were correspondingly higher. The highest protein content was found in the enzymatically processed SPC from the soy flour with additional heat treatment because of the low protein loss and the increased removal of insoluble soy carbohydrate.

TABLE 13

Protein loss percentages and protein contents in collected SPC for 7B grade soy flour without and with additional (2 h) heat treatment and their corresponding enzyme-free processing controls.

| Sample | | | |
|---|---|---|---|
| Additional heat treatment | Enzymatic processing | Protein loss (%) | Protein content in SPC (%) |
| + | − (Control) | 3.9 | 69 |
| + | + | 5.1 | 73 |
| − | − (Control) | 12.3 | 67 |
| − | + | 14.2 | 67 |

The heat treatment is further demonstrated to improve the soy carbohydrate hydrolysis into soluble carbohydrate and monosaccharides. The hydrolysates generated by enzymatic processing of 7B grade soy flour with and without the additional 2 h heat treatment were analyzed carefully. The concentrations of individual sugars measured by using high performance liquid chromatography are given in Table 14, where the sum of these concentrations are also compared with total soluble carbohydrate and reducing sugar measured separately.

TABLE 14

Detailed data of sugar concentrations in hydrolysates generated from enzymatic processing of 7B grade soy flour without and with additional (2 h) heat treatment.

| Sample | Stachyose | Raffinose | Sucrose | Glucose | Xylose | Galactose | Arabinose | Fructose | Unknown Peak | SUM | Total Carbohydrate | Reducing Sugar |
|---|---|---|---|---|---|---|---|---|---|---|---|---|
| with additional heat treatment | 0.0 | 0.0 | 0.0 | 13.7 | 3.20 | 16.9 | 5.04 | 14.7 | 14.0 | 67.6 | 46.2 | 44.7 |
| without additional heat treatment | 0.0 | 0.0 | 0.0 | 12.9 | 3.21 | 12.9 | 2.48 | 14.0 | 11.0 | 56.5 | 40.2 | 40.2 |

Here, the Unknown Peak (which might be galacturonic acid) concentration was estimated using the average calibration of other sugar standards, which was almost the same for all the sugars analyzed. Results showed that the heat treatment improved the yield of soluble carbohydrate and monosaccharides in the enzymatic soy meal processing. Heat treatment is conclusively shown to have very important positive effects on the enzymatic soy meal processing in reducing the protein loss and increasing the hydrolysis of insoluble soy carbohydrate.

Example 14

It was also found that pH is a critically important factor to control and that more effective enzyme mixtures can be produced by allowing a slow decrease of pH over the fermentation. Premature pH decrease to below 6 might negatively affect the desired enzyme production. The specific pH decrease rate may depend on the specific medium composition and cell concentration used.

The hypothesized principle behind the observed results is that the activity of hydrolytic enzyme depends on pH. For the target enzymes for soy carbohydrate hydrolysis, the activities increase as pH is decreased from 7 (but above certain low limits). The increased activities promote faster generation of monomeric carbohydrate from the oligomeric and polymeric carbohydrate. The monomeric carbohydrate is the substrate that the microbial cells can assimilate, for growth and for other metabolic activities including enzyme production. However, if the monomeric carbohydrate is generated too fast, faster than the rate of microbial consumption, it may cause a negative effect on the enzyme production. This negative effect is a feedback regulation mechanism: when the monomeric carbohydrate is already present in a high enough concentration as food to the microbial cells, cells have lower or no incentive (induction) to produce more enzyme for generating more monomeric carbohydrate. The improved enzyme production observed in our experiments with controlled pH decrease is hypothetically due to the better matching between the generation and consumption rates of the monomeric carbohydrate.

pH during the 5 day fermentation period was controlled from 7 to 5. For the first 3 days it was decreased from 7 to 6 at a relatively constant rate; it was then kept constant at pH 6 for 1 day (Day 4) and then decreased to 5 (from 6) during the next day (Day 5). Throughout the fermentation, the dissolved oxygen (DO) level was left to vary naturally (decrease when the cell respiration rate increases, and increase when the cell respiration rate decrease) but pure oxygen was supplemented when necessary to maintain DO over 20% air saturation. Periodical samples were taken for analysis of the activities of different enzymes. Profiles of pectinase and α-galactosidase activities, pH, and DO were determined.

Maximum activities of pectinase and α-galactosidase were both about 8 U/ml. These activities were significantly higher than the activities of 3-4 U/ml pectinase and 2-3 U/ml α-galactosidase using the same medium but without pH control or with different pH control schemes. This pH control with properly scheduled pH decrease to prevent premature decrease to below about pH 6 was found to be effective in increasing the productivity of the two targeted enzymes.

Example 15

In Example 14, it was found that dissolved oxygen (DO) had the tendency to increase after about 1 day. This is thought to be caused by slightly insufficient hydrolysis to generate the monomeric carbohydrate required for active cell metabolism. A further improved fermentation strategy was developed to use the DO profile to guide the pH control so that the monomeric carbohydrate generation rate is sufficient to support the changing cell metabolic activity but not excessive to cause negative effect on the induction for enzyme production. A series of experiments was made to optimize this DO-directed pH control using a control algorithm was developed.

Medium composition and other process conditions were kept the same as the previous experiments, except for the use of the developed DO-directed pH control algorithm. Pectinase production did not stop after 3 days (which was previously observed) and the continued production yielded a final pectinase activity of 11.6 U/ml, significantly higher than the 8 U/ml pectinase activity achieved with the fixed-decrease-rate pH control in the fermentation of Example 14. α-Galactosidase production also increased significantly: the maximum activity was about 8 U/ml in the previous experiment with the fixed-decrease-rate pH control; the activity was 11.6 U/ml in this experiment with the DO-directed pH control.

What is claimed is:
1. A method of hydrolyzing carbohydrates in a protein-rich material comprising the steps of:
   providing, in a first vessel, a supply of a protein-rich material having carbohydrates therein, wherein the entirety of the protein-rich material to be hydrolyzed is provided during the step of providing, such that the method is devoid of a step of adding further protein-rich material;
   adding, after the entirety of the protein-rich material is in the first vessel, a first supply of enzyme broth having an enzyme therein to the first vessel to thereby form a mixture in the first vessel, allowing the enzyme to hydrolyze the carbohydrates to thereby enact a hydrolysis process and form a hydrolyzed mixture;

transferring the hydrolyzed mixture from the first vessel to a second vessel, adding a further supply of additional enzyme broth to the hydrolyzed mixture following the step of transferring, wherein the composition of the further supply of additional enzyme broth is substantially similar to the first supply of enzyme broth; and after said step of adding, allowing an additional hydrolysis process to occur.

2. The method of claim 1, wherein the steps of allowing the enzyme to hydrolyze the carbohydrates and allowing an additional hydrolysis process to occur convert the carbohydrates to soluble carbohydrates, the method further comprising the step of repeating said steps of adding a further supply and allowing an additional hydrolysis process to occur until the conversion of carbohydrates to soluble carbohydrates remains constant.

3. The method of claim 1, the method further comprising the step of repeating said steps of adding a further supply and allowing an additional hydrolysis process to occur until the conversion of the carbohydrates in the protein-rich material to soluble carbohydrates is 65% or higher.

4. The method of claim 1, wherein the enzyme broth further includes a liquid solvent, wherein the liquid solvent is selected from the group consisting of water, sodium citrate buffer, sodium hydroxide, hydrochloric acid, citric acid, ethylene diamine tetra-acetic acid (EDTA), ethanol, methanol, and combinations thereof, wherein the enzyme is selected from the group consisting of cellulase, xylanase, β-glucosidase, cellobiohydrolase, endoglucanase, polygalacturonase, pectinase, pectin lyase, sucrase, α-galactosidase, and combinations thereof.

5. A method of hydrolyzing carbohydrates in a protein-rich material comprising steps of fermenting one or more fungus in a fermentation composition, wherein the step of fermenting includes gradually decreasing the pH of the fermentation composition from 7 to 6 over a first predetermined length of time, wherein the first predetermined length of time is from 1 day to 3 days, maintaining, after the first predetermined length of time, the pH of the fermentation composition at a pH of about 6 for a second predetermined length of time, wherein the second predetermined length of time is from 1 day to 2 days, and gradually decreasing, after the second predetermined length of time, the pH of the fermentation composition from 6 to 5 over a third predetermined length of time, wherein the third predetermined length of time is from 1 day to 3 days, to thereby produce a first supply of enzyme broth having an enzyme therein, wherein the enzyme is selected from the group consisting of cellulase, xylanase, β-glucosidase, cellobiohydrolase, endoglucanase, polygalacturonase, pectinase, pectin lyase, sucrase, α-galactosidase, and combinations thereof, wherein the enzyme broth further includes a liquid solvent, wherein the liquid solvent is selected from the group consisting of water, sodium citrate buffer, sodium hydroxide, hydrochloric acid, citric acid, ethylene diamine tetra-acetic acid (EDTA), ethanol, methanol, and combinations thereof, mixing the first supply of enzyme broth having the enzyme therein and a supply of a soy-based protein-rich material having carbohydrates therein, wherein the entirety of the soy-based protein-rich material to be hydrolyzed is provided during the step of mixing, such that the method is devoid of a step of adding further soy-based protein-rich material;

allowing the enzyme to hydrolyze the carbohydrates to thereby enact a hydrolysis process and form a hydrolyzed mixture;

adding a further supply of additional enzyme broth to the hydrolyzed mixture following the step of allowing the enzyme to hydrolyze the carbohydrates, wherein the composition of the further supply of additional enzyme broth is substantially similar to the first supply of enzyme broth.

6. A method of hydrolyzing carbohydrates in a protein-rich material comprising the steps of:

providing a mixture of an enzyme broth and a protein-rich material having carbohydrates therein, the enzyme broth including a mixture of enzyme components including a to-be-accumulated enzyme component selected from the group consisting of α-galactosidase, sucrase, β-glucosidase, and combinations thereof;

allowing the mixture of enzyme components to hydrolyze the carbohydrates to thereby produce a product stream;

separating the product stream into a protein concentrated stream and a liquid hydrolysate stream;

separating the liquid hydrolysate stream into a collected hydrolysate stream and a to-be-recycled enzyme stream consisting essentially of the to-be-accumulated enzyme component;

collecting the collected hydrolysate stream;

collecting the protein concentrated stream; and recycling the to-be-recycled enzyme stream by combining the to-be-recycled enzyme stream with additional protein-rich material and additional enzyme broth to form a recycled enzyme mixture, thereby preferentially accumulating the to-be-accumulated enzyme component in the recycled enzyme mixture to thereby avoid the undesirable production of oligomers from the additional protein-rich material.

7. The method of claim 6, wherein said step of combining includes steps of continuously adding the enzyme broth and continuously adding the protein-rich material, the method further comprising the step of continuously removing the product stream.

8. The method of claim 6, wherein the protein-rich material is a soy based material selected from the group consisting of soy flour, soybean meal, soy protein concentrate, soybean hulls, soy flake, white flake, spent soy flake, soybean cake, soybean oil cake, soy molasses, okara, soy pulp, soy bran, soy isolate fiber, and combinations thereof.

9. The method of claim 6, wherein the mixture of enzyme components is selected from combinations of the group consisting of cellulase, xylanase, β-glucosidase, cellobiohydrolase, endoglucanase, polygalacturonase, pectinase, pectin lyase, sucrose, α-galactosidase.

10. The method of claim 1, further comprising a step of dry heating or dry toasting the supply of the protein-rich material prior to said step of providing, where said step of dry heating or dry toasting occurs at a temperature of from 150° C. to 200° C.

11. The method of claim 1, wherein the protein-rich material is present at a concentration of from 100 g/L to 350 g/L.

12. The method of claim 1, further comprising steps of
prior to said step of providing the mixture, providing, at room temperature, the supply of the protein-rich material which supply of the protein-rich material has been heat processed, and
after said step of providing the supply of the protein-rich material, dry heating or dry toasting the supply of the protein-rich material prior to said step of providing the mixture, where said step of dry heating or dry toasting occurs at a temperature of from 100° C. to 250° C.

13. The method of claim 1, wherein the method achieves a carbohydrate conversion of at least 4% more than a corresponding method without the step of adding a further supply of additional enzyme.

14. The method of claim 1, wherein the method utilizes a total amount of enzyme, wherein the first supply of enzyme broth provides about 20%, about 25%, or about 33⅓% of the total amount of enzyme, and wherein the further supply of additional enzyme broth provides the same total amount of enzyme as the first supply of enzyme broth.

15. The method of claim 6, the method consisting of said steps of providing the mixture, allowing the mixture, separating the product stream, separating the liquid hydrolysate stream, collecting the collected hydrolysate stream, collecting the protein concentrated stream, and recycling the to-be-recycled enzyme stream.

* * * * *